US012582997B2

(12) United States Patent
Sharma et al.

(10) Patent No.: US 12,582,997 B2
(45) Date of Patent: Mar. 24, 2026

(54) DEVICE FOR MANIPULATING MAGNETIC BEADS AND ASSAY METHOD

(71) Applicant: LUMINULTRA TECHNOLOGIES LTD., Fredericton (CA)

(72) Inventors: Neil Christopher Sharma, Gaithersburg, MD (US); Noah Chamberlain Todd, Baltimore, MD (US); Michael James Witman, Sparks, MD (US)

(73) Assignee: LUMINULTRA TECHNOLOGIES LTD., Fredericton (CA)

( * ) Notice: Subject to any disclaimer, the term of this patent is extended or adjusted under 35 U.S.C. 154(b) by 1030 days.

(21) Appl. No.: 17/590,497

(22) Filed: Feb. 1, 2022

(65) Prior Publication Data

US 2022/0241798 A1 Aug. 4, 2022

Related U.S. Application Data

(60) Provisional application No. 63/144,736, filed on Feb. 2, 2021.

(51) Int. Cl.
B03C 1/28 (2006.01)
B03C 1/01 (2006.01)
(Continued)

(52) U.S. Cl.
CPC ................ B03C 1/288 (2013.01); B03C 1/01 (2013.01); B03C 1/286 (2013.01); G01N 1/405 (2013.01);
(Continued)

(58) Field of Classification Search
CPC ..... B03C 1/286; B03C 1/288; B03C 2201/18; B03C 2201/26; B01L 3/563; B01L 3/50825; B01L 2300/046
(Continued)

(56) References Cited

U.S. PATENT DOCUMENTS 5,542,562 A * 8/1996 Oratz ..................... A47G 19/22
220/23.86
10,053,277 B2 * 8/2018 Rahmel .................. B65D 43/02
(Continued)

FOREIGN PATENT DOCUMENTS

JP 2012-110279 A 6/2012
KR 101734377 B1 * 5/2017 ......... C12N 15/1013

OTHER PUBLICATIONS

Harayama; Shigeaki, "Device for Moving Magnetic Beads" (English Translation), Jun. 14, 2012, worldwide.espacenet.com (Year: 2012).*

(Continued)

*Primary Examiner* — Molly K Devine

(57) ABSTRACT

Various devices are described for separating magnetic beads from a suspension in a tube. The devices allow a magnet to be placed near, or removed from, a cap associated with the tube. Magnetic beads can be attached to the cap by holding the tube such that the suspension flows onto an inner surface of the cap. The cap may be removed and replaced on a tube or moved to a different tube. Removing the device, or a magnet of the device, allows the magnetic beads to be released into a liquid in a tube. In a kit, a plurality of tubes may be pre-filled with reagents for an assay. In a process, the device can be used to move magnetic beads from one tube to another. Other devices and process are described for separating magnetic beads from liquid in a syringe or flowing into or out of a syringe.

12 Claims, 20 Drawing Sheets

(51) Int. Cl.
  *G01N 1/40*        (2006.01)
  *G01N 33/543*      (2006.01)
(52) U.S. Cl.
  CPC ...... *G01N 33/5434* (2013.01); *B03C 2201/18*
                               (2013.01)
(58) Field of Classification Search
  USPC .............................. 209/39, 223.2, 224; 435/5
  See application file for complete search history.

(56)                  References Cited

U.S. PATENT DOCUMENTS

2012/0322052 A1*  12/2012  Halverson ................ G01N 1/18
                                                    435/5
2015/0196905 A1*  7/2015  Pinard ................... B01L 3/5021
                                                    422/548
2018/0127741 A1*  5/2018  Feistel ...................... B03C 1/30

OTHER PUBLICATIONS

Min; Jun Hong, "Nucleic Acid Extracting Kit and Nucleic Acid Extracting Method Utilizing It" (English Translation), May 15, 2017, worldwide.espacenet.com (Year: 2017).*
V&P Scientific, Inc., "Magnetic Racks for Tubes—Magnetic Bead Separation Devices—Products", http://vp-sci.com/products/magnetic-bead-separation-devices/magnetic-racks-for-tubes.html; accessed Jun. 2, 2022, 6 pages.
Thermofisher Scientific, "KingFisher Flex Magnetic Particle Processor", https://www.thermofisher.com/us/en/home/life-science/bioproduction/contaminant-and-impurity-testing/sample-prep-and-automation/kingfisher-flex-magnetic-particle-processor.html; accessed Jun. 2, 2022, 3 pages.
Permagen Labware, "2x 15ml Centrifuge Tube Magnetic Separation Rack MSR2X15", 2015, 1 page.

* cited by examiner

14

10

DEVICE FOR MANIPULATING MAGNETIC BEADS AND ASSAY METHOD

CROSS-REFERENCE TO RELATED APPLICATIONS

This application claims the benefit of U.S. Provisional Patent Application No. 63/144,736, filed Feb. 2, 2021, which is incorporated herein by reference.

FIELD

This specification relates to devices for manipulating magnetic beads in biological assays, for example to separate nucleic acids or other materials from a sample, and to bioassay methods using magnetic beads, for example to detect nucleic acids from viruses or bacteria in a liquid sample.

BACKGROUND

Magnetic beads are used in a variety of assays including, for example, molecular biology applications such as purifying nucleic acids and antibody pull-down assays. Working with magnetic beads requires the ability to separate the beads from the surrounding solution (i.e. reagent and/or sample) when necessary, for example to allow for washing the magnetic beads with additional buffers or for eluting the target biomolecules or other materials from the magnetic beads. Current devices for manipulating magnetic beads primarily fall into two categories: magnetic tube racks for manual processing of samples; and, automated instruments.

With magnetic tube racks, a tube or microplate holding a liquid sample including magnetic beads is placed into the rack next to a magnet that is embedded in the rack. The beads collect near the bottom of the tube or plate adjacent to the magnet and then the solution is pipetted or poured off before adding additional solutions. The tube or plate can be removed from the magnetic tube rack to release the magnetic beads back for re-suspending the magnetic beads in a solution.

Automated instruments are used in laboratories—particularly clinical laboratories—for processing large numbers of samples using magnetic beads. Typically, liquid samples are first placed into deep 96-well plates and magnetic beads are suspended in the liquid. Magnetic rods that are covered with a disposable plastic cover are dipped into the wells to collect the magnetic beads onto the rods. The rods—with collected beads—are then transferred by a mechanism of the instrument to a second well plate containing the next solution used in the assay process. The magnetic rods are subsequently retracted from the plastic covers by another mechanism of the instrument and the beads are released into the wells of the second well plate. This collection and release process can be repeated as required to complete an assay.

INTRODUCTION

The following introduction is intended to introduce the reader to the detailed description and the claims to follow but is not intended to limit or define the claims.

Automated instruments can be powerful but they are not portable for field-based or point-of-need applications, and not suitable for processing one or a small number of samples. Magnetic tube racks are portable but they are intended for use by a skilled technician in a laboratory. When using a magnetic tube rack, the technician typically pipets or pours off a first liquid from a tube after collecting the magnetic beads in the magnetic rack before adding a second liquid to the tube. This can create a disposal problem in the field or at a point-of-need. Further, the amount of the second liquid must be carefully measured and, in some cases, a small amount of a first solution can remain in a tube and contaminate a second reagent added to the tube.

This specification describes a device for manipulating magnetic beads. The device includes a magnet and can be selectively attached to a sampling device, such as a tube, or removed from the sampling device. In some examples, the device attaches to the cap of a tube, for example a conical centrifuge or microcentrifuge tube, a round bottom test tube, or a cylindrical vial. In some examples, the device attaches to the tube of a syringe. When used with a cap, the cap can be removed from a tube and placed on a tube with the device attached to the cap.

This specification also describes a process for manipulating magnetic beads. In some examples, a first solution and magnetic beads are placed in a tube and a cap is attached to the tube. A device including a magnet is attached to the cap, either before or after attaching the cap to the tube. The tube is inverted to collect the magnetic beads on the cap. The tube is later returned to an upright position to separate the first solution from the magnetic beads. Optionally, the cap can then be removed from the tube with the device and the magnetic beads still attached to the cap. The first solution can be replaced with a second solution (which may be the same type of solution as the first solutions or a new type of solution) and the cap is replaced on the tube, or the cap can be placed on another tube containing the second solution. Removing the device or the magnetic component of the device allows the beads to be released into the second solution. This process of collecting beads on the cap and releasing beads from the cap can be repeated with additional solutions as required by a bioassay. For example, the process may be used to separate nucleic acids from a sample. Optionally, a liquid may be added to or removed from the magnetic beads, for example by pipette or by evaporation, while the magnetic beads are attached to the cap but the cap is not attached to the tube.

In some examples, a device and/or process described herein allows a sample to be processed with less need for pipetting or pouring off solutions or measuring solutions in the field. Optionally, tubes can be pre-filled with solutions (i.e. buffers or other reagents) at a facility (i.e. a factory or laboratory) with safe and accurate material handling equipment and sent for use in the field or at a point-of-need. A nucleic acid collection kit, for example, can include tubes pre-filled with different bead processing solutions, for example a lysis buffer, a wash buffer or an elution buffer, in amounts predetermined for use in a particular assay. Once a tube is used in one step of the assay, it can be capped and returned to a facility for the safe disposal, storage or further testing of its contents, and optionally for the recovery of the tube for re-use. A clean tube, with no residual substances from a prior step, can be used for a subsequent assay process step.

Even without automated equipment, the device and/or process described herein can be used in the field or at the point-of-need by an operator with minimal skills and additional equipment. The device and/or process can also be used in a laboratory. In some examples, special plastic ware is not required since the magnetic devices can be configured to work with existing commonly used tubes and caps. Alternatively, special plasticware could be used.

DETAILED DESCRIPTION

FIGS. 1 to 8 show various devices for separating and/or transferring magnetic beads in a chemical or biological assay. Magnetic beads are typically about 0.5 to 500 micrometers in diameter and may also be called microbeads or Ugelstad particles. The magnetic beads have one or more magnetic core particles surrounded by, or dispersed in, one or more other materials. In some examples, the core particles are made of a ferromagnetic, ferrimagnetic, paramagnetic or superparamagnetic material. For example, magnetic beads may have core particles made of an iron oxide such as magnetite. Magnetic beads with paramagnetic or superparamagnetic core particles are not attracted to metals while subjected to a magnetic field and do not stay magnetized in the absence of an external magnetic field. Magnetic beads can be separated from a suspension by applying a magnetic field to the suspension, typically by placing a magnet near the suspension. Other materials in the magnetic bead are adapted to bind to a target of interest. In some examples the binding is reversible. For example, silica coated magnetic beads reversibly bind nucleic acids based on salt concentration.

Figures 1A, 1B:
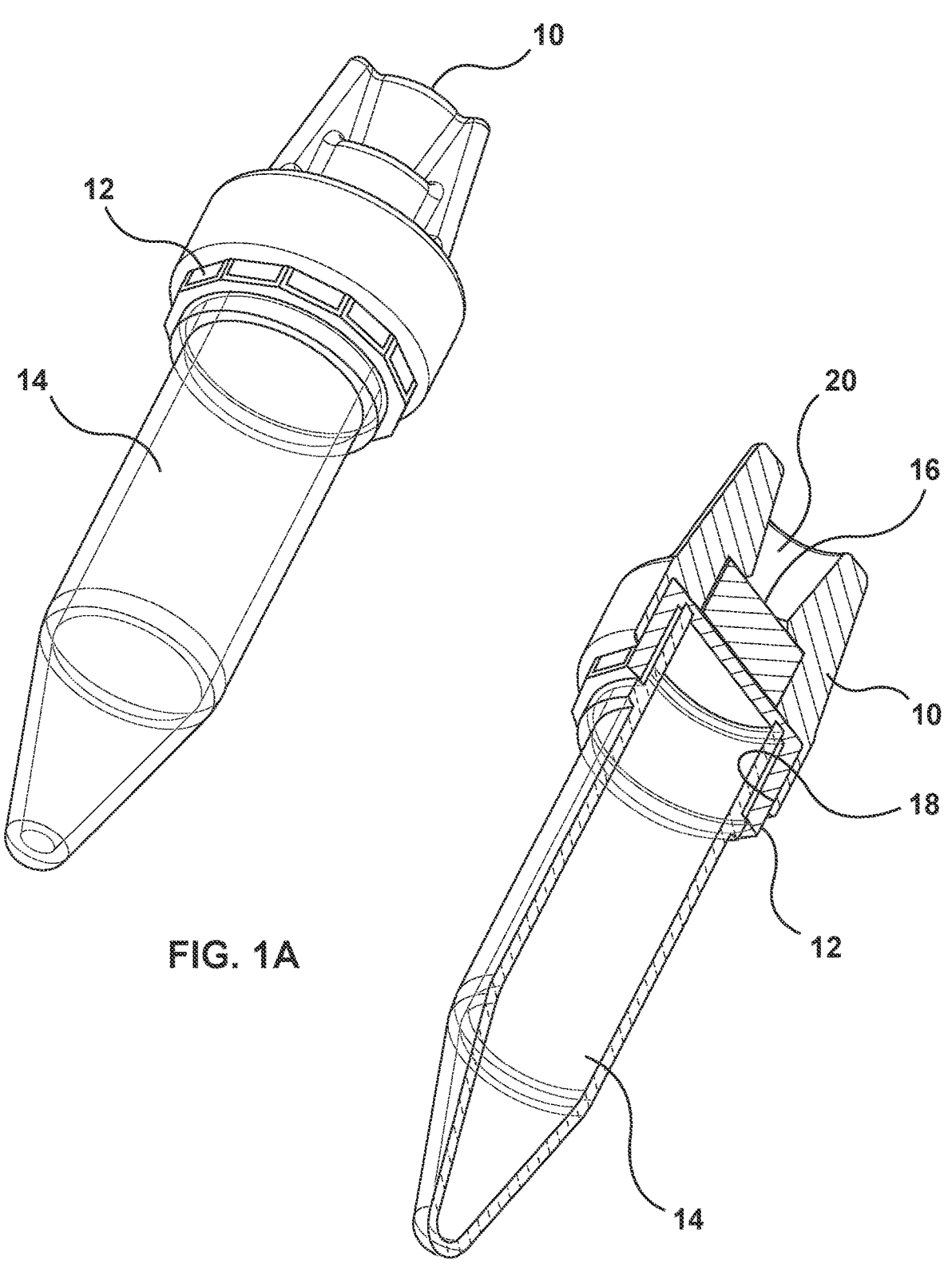
FIG. 1A shows an isometric view of a first sleeve on the screw cap of a conical centrifuge tube.
FIG. 1B is a cross section of the sleeve, cap and tube of FIG. 1B.
Figure 1C:
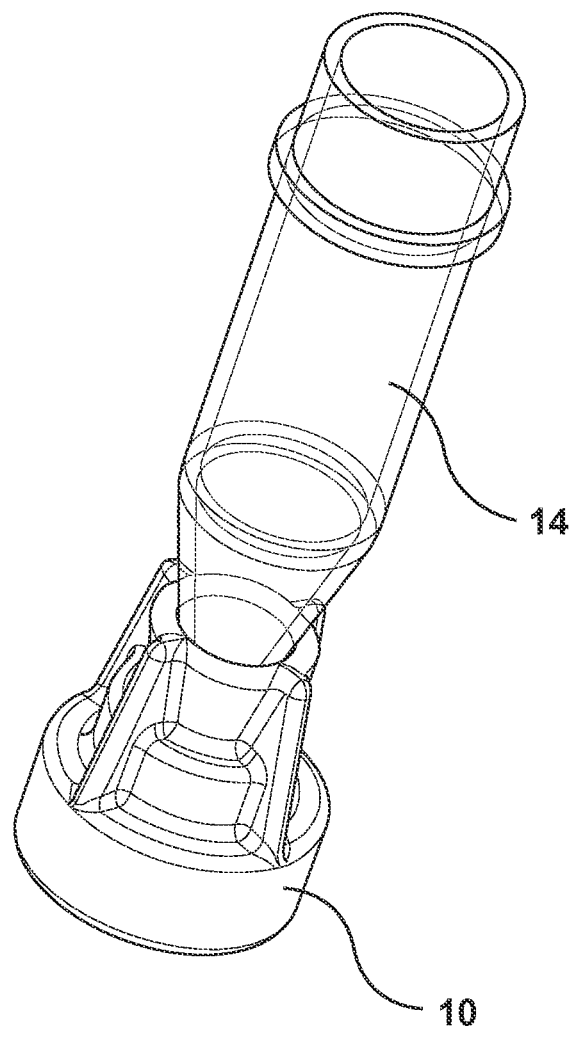
FIG. 1C is an isometric view of the sleeve of FIG. 1A placed on the conical end of a centrifuge tube.

FIG. 1A shows an isometric view of a first sleeve 10. The first sleeve 10 has a first recess 18 that fits over some or all of an external cap 12 on a tube 14. The word "sleeve" is used in the sense of a connecting fitting over or enclosing the cap 12 but part of the sleeve 10 may also extend beyond the cap 12. External cap 12 is called "external" because a sidewall of the external cap 12 fits over the outside of the sidewall of tube 14, although other parts of the external cap 12 may extend into a tube 14. For example, the external cap 12 may also have an inner sidewall (not shown in FIG. 1B but commonly provided in commercially available external caps 12) that extends into tube 14 against the inside of the sidewall of tube 14. The tube 14 may be any standard or custom made size, for example 5 mL, 15 mL or 50 mL. In the example shown, the tube 14 is a conical tube of the type commonly used in a centrifuge, for example an EPPEN-DORF™ tube. Tube 14 may be made, for example, of polypropylene, polystyrene, or another material. In the example shown, the external cap 12 is a threaded cap that can be screwed onto or off of a tube 14. Alternatively the sleeve 10 may be adapted for use with tubes of other types (i.e. round bottomed test tubes or cylindrical vials), shapes or sizes and/or caps of other types (i.e. a snap cap or flip cap), shapes or sizes.

The external cap 12 can be attached to a tube 14 or removed from a tube 14 while the first sleeve 10 is on the external cap 12. In the example shown, the first sleeve 10 is made of an elastic material, such as silicone or rubber. The first recess 18 of the elastic first sleeve 10 is sized such that first sleeve 10 is stretched over and grips the sides of the external cap 12. Alternatively, a first sleeve 10 may be made of a generally rigid material, such as a plastic, and the first recess 18 may have a press fit or click fit with the external cap 12. In the example of a threaded external cap 12, rotating the first sleeve 10 also rotates the external cap 12 and lifting the first sleeve 10 also lifts the external cap 12.

Referring to FIG. 1B, the first sleeve 10 contains a magnet 16. When the first sleeve 10 is placed on the external cap 12, the magnet 16 is near, but outside of, the external cap 12. In the example shown, the magnet 16 can be placed against the outer surface of the top of the external cap 12. If the tube 14 contains a suspension of magnetic beads, inverting the tube 14 allows the magnetic beads to collect against an inner surface of the external cap 12. When the tube 14 is rotated back to an upright position, the magnetic beads remain attached to the inner surface of the external cap 12 while the liquid falls back to the bottom of the tube 14. In this way, the magnetic beads can be separated from a suspension. The external cap 12 can also be removed from the tube 14 with the magnetic beads still attached to the external cap 12. Optionally, the tube 14 can be emptied of a first solution and filled with a second solution while the magnetic beads are attached to the cap, or a second tube 14 containing the second solution can be provided. The second solution may be a fresh quantity of the same type as the first solution or a different type of solution. The second tube 14, if used, may the same as the first tube 14 or a different type, size or shape of tube 14. The external cap 12 with magnetic beads attached to it can be placed on the re-filled tube 14 or the second tube 14. Removing the first sleeve 10 from the external cap 12 releases the magnetic beads from the external cap 12 into the second solution.

Figure 10:
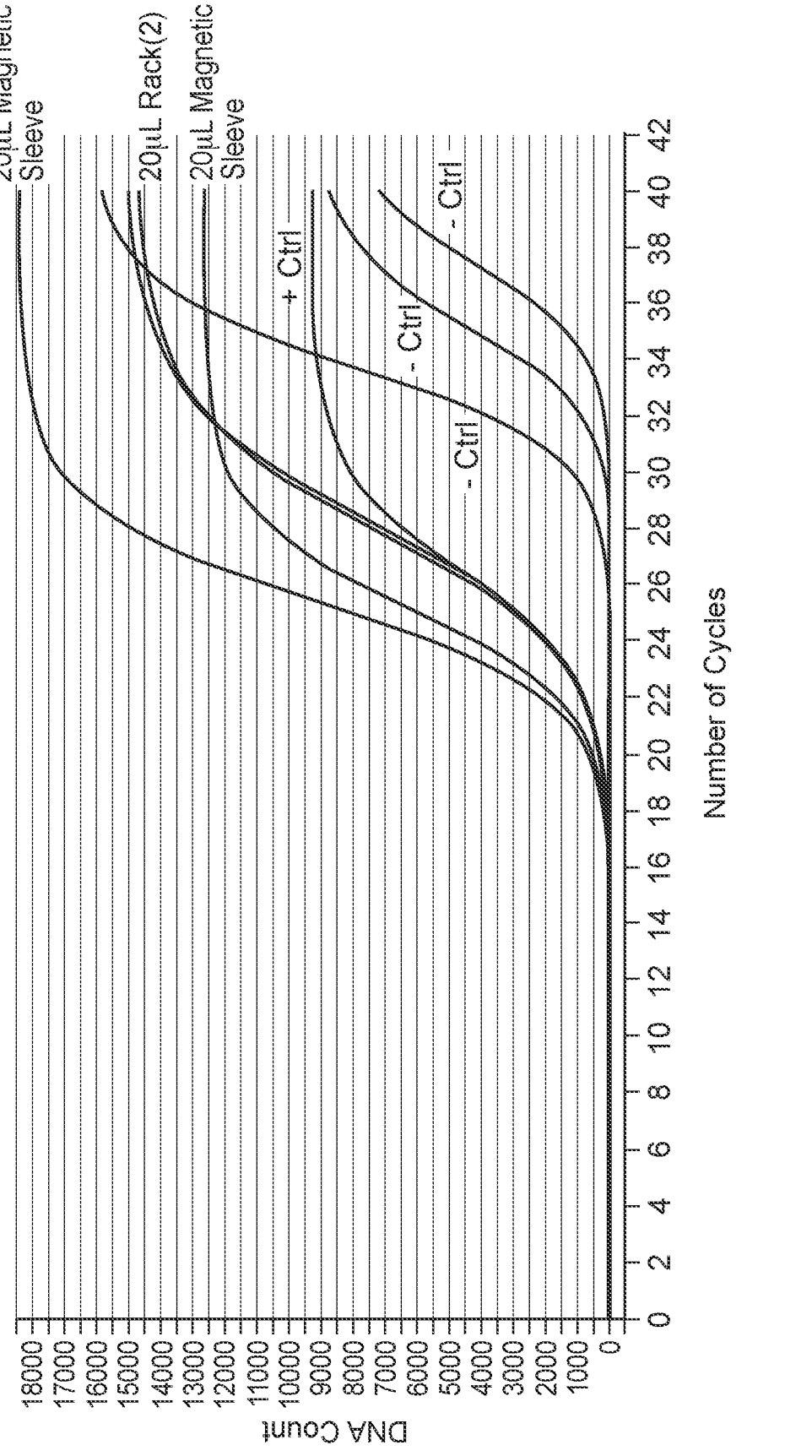
FIG. 10 is a graph of experimental results showing counts of total prokaryote DNA over a number of qPCR cycles for DNA extracted from corn mash samples using silica-coated magnetic beads, comparing samples processed using a magnetic sleeve as in FIG. 1 and samples processed using a traditional magnetic rack.

As shown in FIG. 1B, the first sleeve 10 optionally has a second recess 20. As shown in FIG. 10, the second recess 20 has a size and shape adapted to accept the permanently closed end of a tube (i.e. the end of a tube that is not open and is not closed with a cap) to a position near the magnet 16. In the example shown, the second recess 20 accepts the conical end of the tube 14, or the end of similar tube of a different size having a similar conical end. In other examples, the second recess 20 may be adapted to accept the permanently closed end of a tube with a different shape, for example a hemi-spherical or cylindrical shape. Alternatively or additionally, the second recess 20 may be adapted to accept a tube of a different size class. For example, whereas the first recess 18 in the example shown in FIG. 1A fits on the screw cap 12 of a 5 mL or more conical centrifuge tube, the second recess 20 may accept the conical end of a micro-centrifuge tube, for example of 2 mL or less. The second recess 20 can be used to separate magnetic beads from a suspension and hold the magnetic beads at the permanently closed end of a tube inserted into the second recess 20. Liquid can be poured out of a tube 14 inserted into the second recess 20 to separate the liquid from magnetic beads held in the permanently closed end of the tube 14.

In another option, the second recess 20 may accept a cap of a different type, for example a flip cap, and/or a cap of a different size than the cap associated with the first recess 18.

In the example shown, the recesses 18, 20 of the first sleeve 10 allow a cap 12 or the permanently closed end of a tube 14 to contact the magnet 16 directly. Alternatively, the sleeve 10 may have a layer of material, or produce a gap, separating the magnet 16 from the first recess 18 or the second recess 20. Optionally, the layer of material or gap is thin enough in relation to the strength of the magnet 16 and/or the selected magnetic beads such that magnetic beads can still be separated from a suspension in the tube 14.

Referring the FIG. 10, the first sleeve 10 can also be used as a stand to hold a tube 14 inserted into one of the recesses 18, 20. In the example shown, the first sleeve 10 can be used to hold a conical tube 14 upright. Optionally, the magnet 16 may be separated from the second recess 20 by a sufficient gap or thickness of material, relative to the strength of the magnet 16 and/or selected magnetic beads, such that magnetic beads in the tube 14 are not separated from a solution in a tube 14 inserted into the second recess 20. Alternatively, an external cap 12 removed from the tube 14 can be held or placed on a surface with the first recess pointing upwards. In this orientation, a liquid may be added to or removed from the magnetic beads, for example by pipette or by evaporation, while the magnetic beads are attached to the external cap 12 but the external cap 12 is not attached to the tube 14.

Figures 2A, 2B:
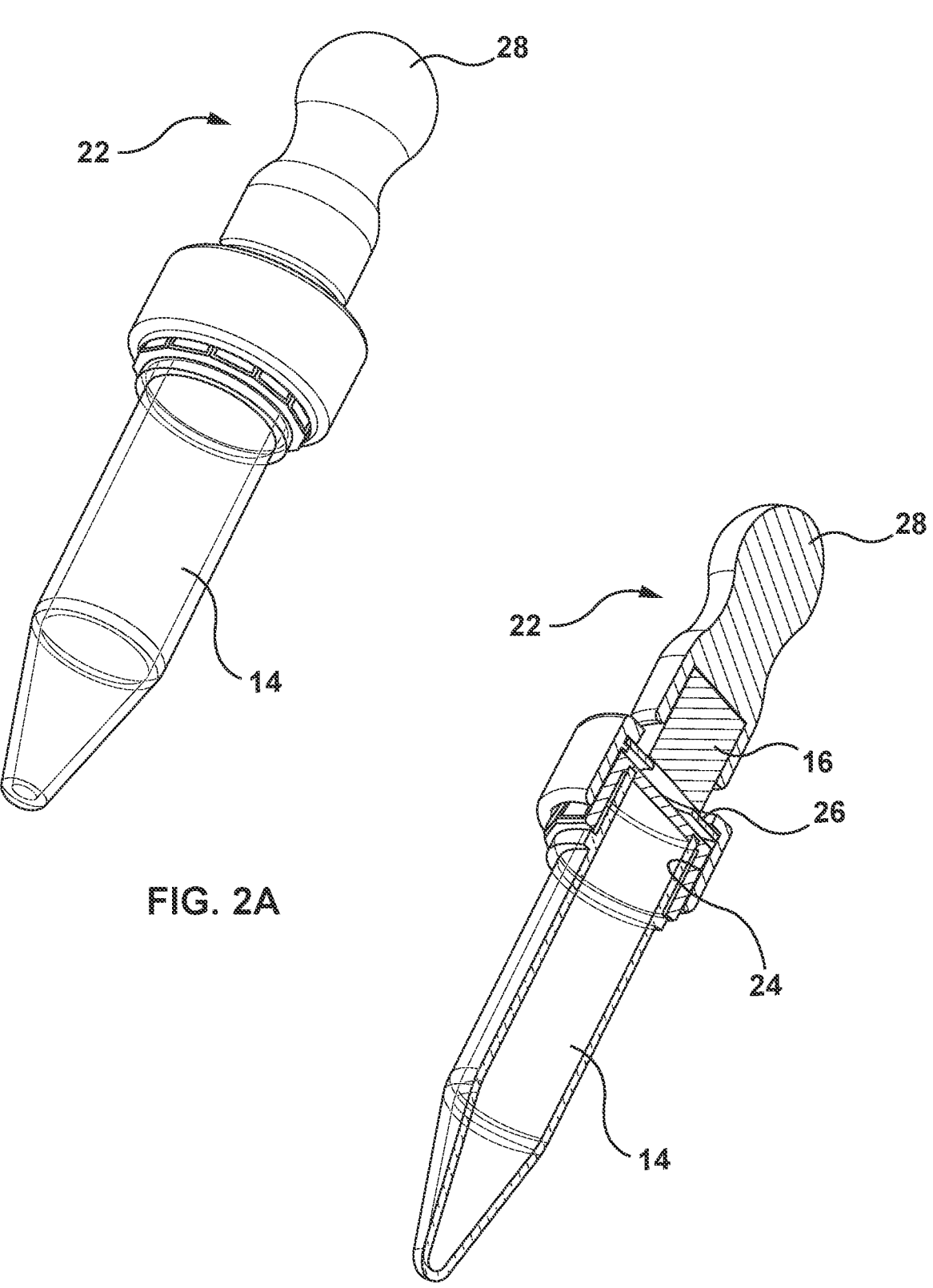
FIG. 2A shows an isometric view of a second sleeve and magnet holder on the screw cap of a conical centrifuge tube.
FIG. 2B is a cross section of the sleeve, holder, cap and tube of FIG. 2A.

FIG. 2A shows an isometric view of a second sleeve 22. The second sleeve 22 has a recess 24 that fits over some or all of the external cap 12 of a tube 14. The external cap 12 and tube 14 may be as described above. Alternatively the second sleeve 22 may be adapted for use with tubes of other shapes, sizes or cap types.

The external cap 12 can be placed onto a tube 14 or removed from a tube 14 while the second sleeve 22 is on the screw cap 12. In the example shown, the second sleeve 22 is made of an elastic material, such as silicone or rubber. The recess 24 of the elastic second sleeve 22 is sized such that it stretches over and grips the sides of the external cap 12. Alternatively, a second sleeve 22 may be made of a generally rigid material, such as a plastic, and the recess 24 may have a press fit or click fit with the external cap 12.

Figure 2C:
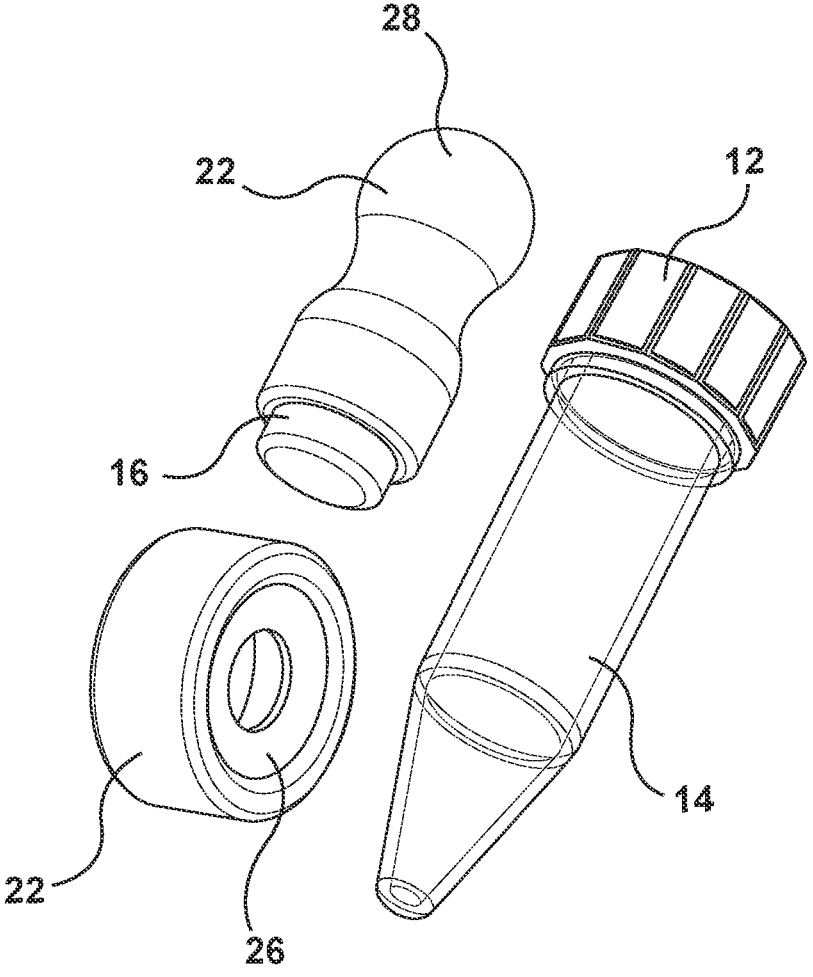
FIG. 2C is an exploded view of the assembly of FIG. 2A.

Referring to FIGS. 2B and 2C, the second sleeve 22 contains a metal insert 26. The metal insert 26 may be in the shape of a ring as shown or optionally in another shape, for example a disc or rod. A magnet 16 can be attached or placed near the metal insert 26 to temporarily magnetize the metal insert 26 and produce a magnetic field near the external cap 12. The metal insert 26 is de-magnetized when the magnet 16 is removed. Optionally, a magnet holder 28 may be used to hold the magnet 16 while providing a handle to make it easier to remove or replace the magnet 16. Alternatively, rather than or in addition to attachment to the metal insert 26, a removable magnet 16 may be screwed, snapped, pushed or otherwise placed into a sleeve 10, 22 or other device.

When the second sleeve 22 is placed on the screw cap 12, the metal insert 26 is near the external cap 12. In the example shown, the metal insert 26 can be placed against, or a short distance (i.e. 3 mm or less) away from the outer surface of the top of the external cap 12. If the tube 14 contains a suspension of magnetic beads, inverting the tube 14 while the magnet 16 is near or against the metal insert 26 allows the magnetic beads to collect against an inner surface of the top of the external cap 12. When the tube 14 is rotated again to an upright position, the magnetic beads remain attached to the inner surface of the top of the external cap 12 while the liquid falls back to the bottom of the tube 14. Removing the second sleeve 22 from the external cap 12, or removing the magnet 16 from the second sleeve 22, releases the magnetic beads from the external cap 12. In this way, as described above, the magnetic beads can be separated from a first solution and, optionally, transferred to a second solution.

Figure 3:
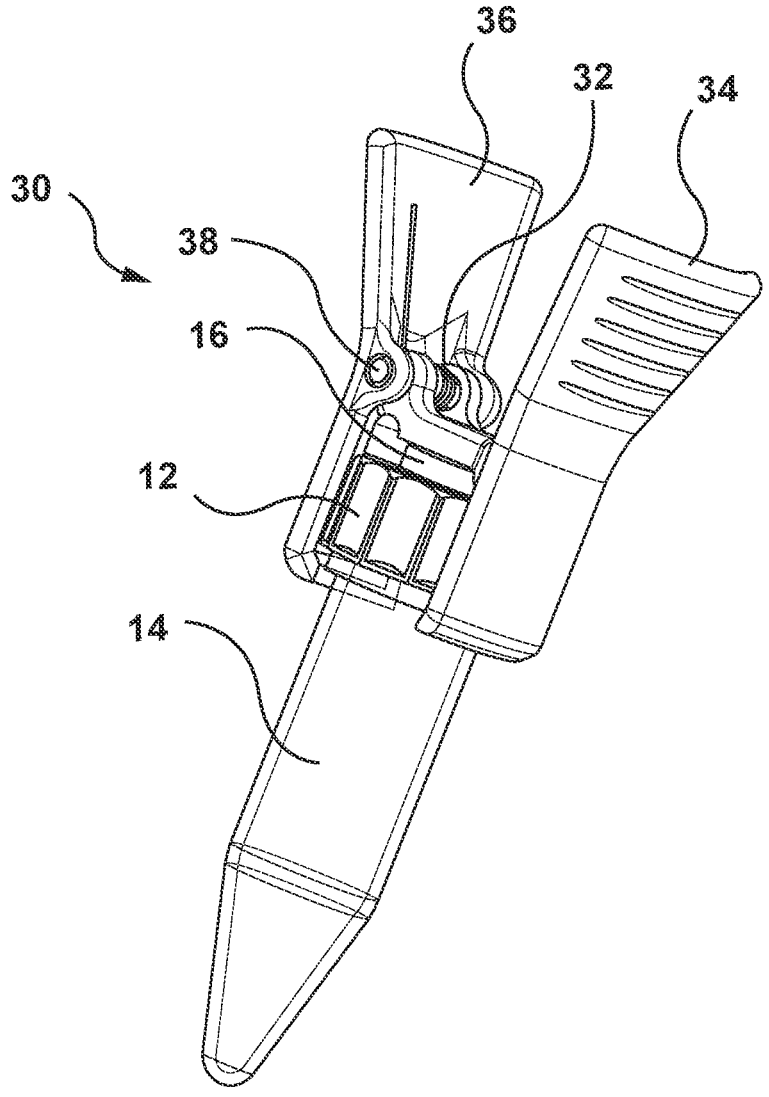
FIG. 3 shows an isometric view of a spring clamp for holding a magnet on the screw cap of a conical centrifuge tube.

FIG. 3 shows a clamp 30 for temporarily holding a magnet 16 near an external cap 12 on a tube 14. The clamp 30 has a first part 34 and a second part 36 held together by a pin 38. In the position shown, a spring 32 biases parts of the clamp 30 against the sides of the external cap 12. In this position, the first part 34 of the clamp 30 holds a magnet 16 near or against the outer surface of the top of the external cap 12. With the clamp 30 attached to the external cap 12, the external cap 12 can be removed from a tube 14 or placed onto a tube 14. However, a person can also squeeze the clamp 30 against the bias of the spring 32 to release the clamp 30 from the external cap 12. The clamp 30 can then be removed from the external cap 12, which causes the magnet 16 to also be removed from the external cap 12. Magnetic beads can be attached to or released from an inner surface of the external cap. As described above, the magnetic beads can be separated from a first solution and, optionally, transferred to a second solution.

The devices in FIGS. 1-3 are shown as used with a cap, for example a screw cap, that has not been modified from a form that is commonly used and commercially available. Alternatively, a novel cap could be created. For example, a cap could have a sidewall extending from the top of the cap along the inside surfaces of the wall of the tube 14 to contain the magnetic beads within the inner diameter of the tube 14. Optionally, a commercially available cap having such an internal sidewall may be used. In another example, the top of a cap could have a recess or indent such that a magnet 16 or metal insert 26 could extend from the top of the cap into the tube 14 (though not so far into the tube 14 that the cap would touch liquid, for example a nominal full volume of liquid, in the tube 14) to concentrate magnetic beads towards the center of the cap. However, in at least some assays, neither of these options appears to be necessary to separate magnetic beads from a solution in one tube 14, transfer the magnetic beads to another tube 14, and release the magnetic beads into a solution in the other tube 14.

Figures 4A, 4B, 4C:
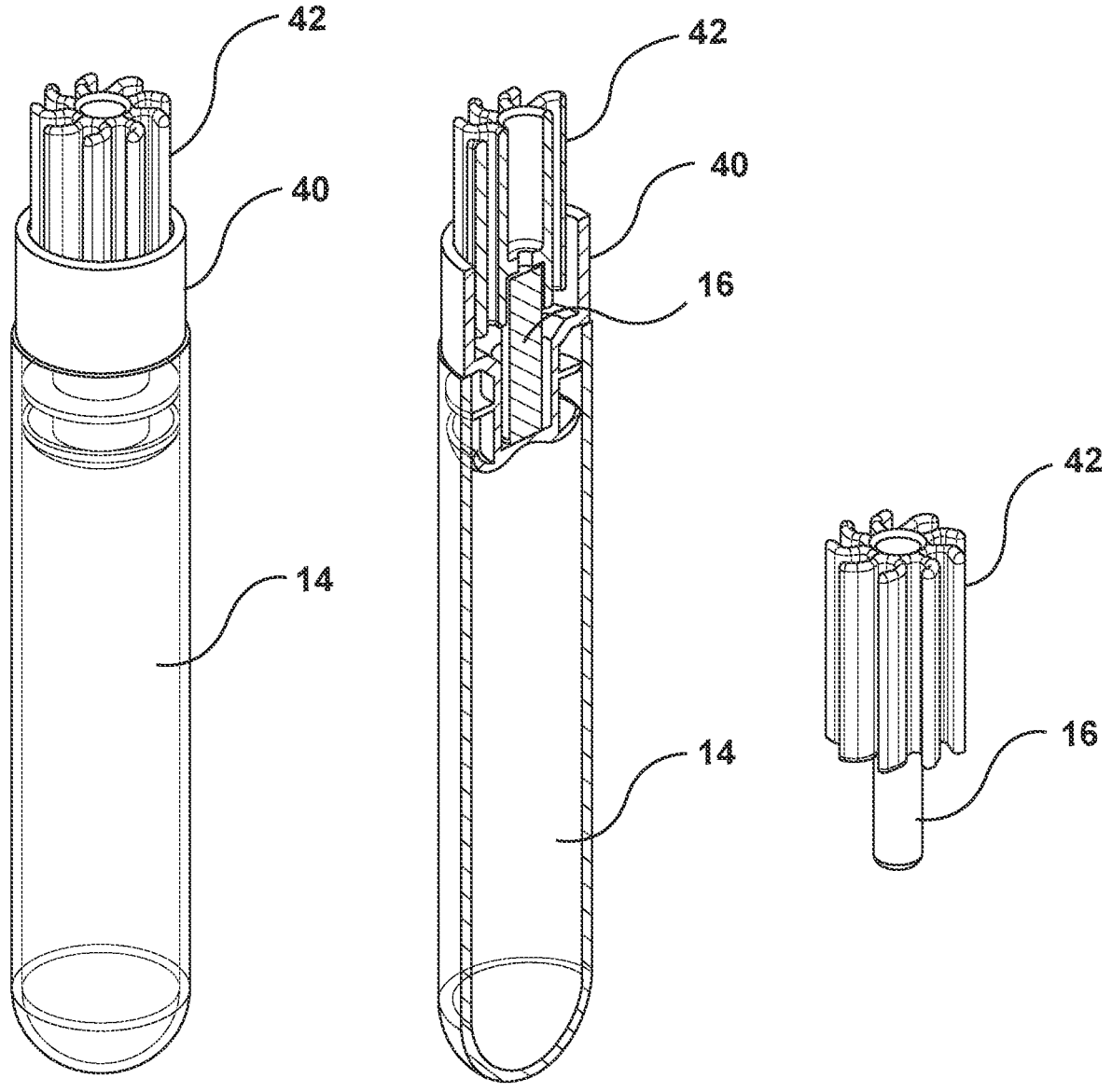
FIG. 4A shows an isometric view of a first insert in a push cap of a round bottom test tube.
FIG. 4B is a cross section of the insert, cap and tube of FIG. 4A.
FIG. 4C is an isometric view of the first insert of FIG. 4A removed from the cap.

FIGS. 4A and 4B show a tube 14 with an internal cap 40 and a first insert 42. The internal cap 40 is described as "internal" because sidewalls of the internal cap 40 are placed against the inside surface of the sidewalls of tube 14. However, as for the push cap shown, part of the internal cap 40 may also extend outside of the tube 14. In the example shown, the tube 14 is a round bottom test tube, for example 12 mm*55 mm or 12 mm*75 mm. Tube 14 may be made, for example, of polypropylene, polystyrene, or another material. Alternatively the first insert 42 may be adapted for use with tubes of other types, shapes or sizes and/or caps of other types, shapes or sizes.

Referring also to FIG. 4C, the first insert 42 is attached to a magnet 16. The first insert 42 can be placed in the internal cap 40, which causes the magnet 16 to also be inserted into the internal cap 40. In the example shown, the first insert 42 is elastic. A part of the first insert 42 compresses as it enters the internal cap 40 to hold the first insert 42 in place. Another part of the first insert 42 remains outside of the internal cap 40 to provide a hand-hold for inserting and removing the first insert 42. With the first insert 42 in place, at least part of the internal cap 40 is also accessible to a user's hands such that the internal cap 40 can also be attached to a tube 14 or removed from a tube 14 while the first insert 42 is in place.

As described above, when the first insert 42 is in place in the internal cap 40, inverting a tube 14 with a suspension of magnetic beads causes the magnetic beads to be attached to the internal cap 40. Returning the tube 14 to an upright position causes the magnetic beads to be separated from the suspension. The internal cap 40 can be removed from a tube 14 and placed on a tube 14 with the magnetic beads attached to the internal cap 40. Removing the first insert 42 from the internal cap 40 releases magnetic beads into a tube 14. Magnetic beads can be separated from a first solution and, optionally, transferred to a second solution.

Figure 5A:
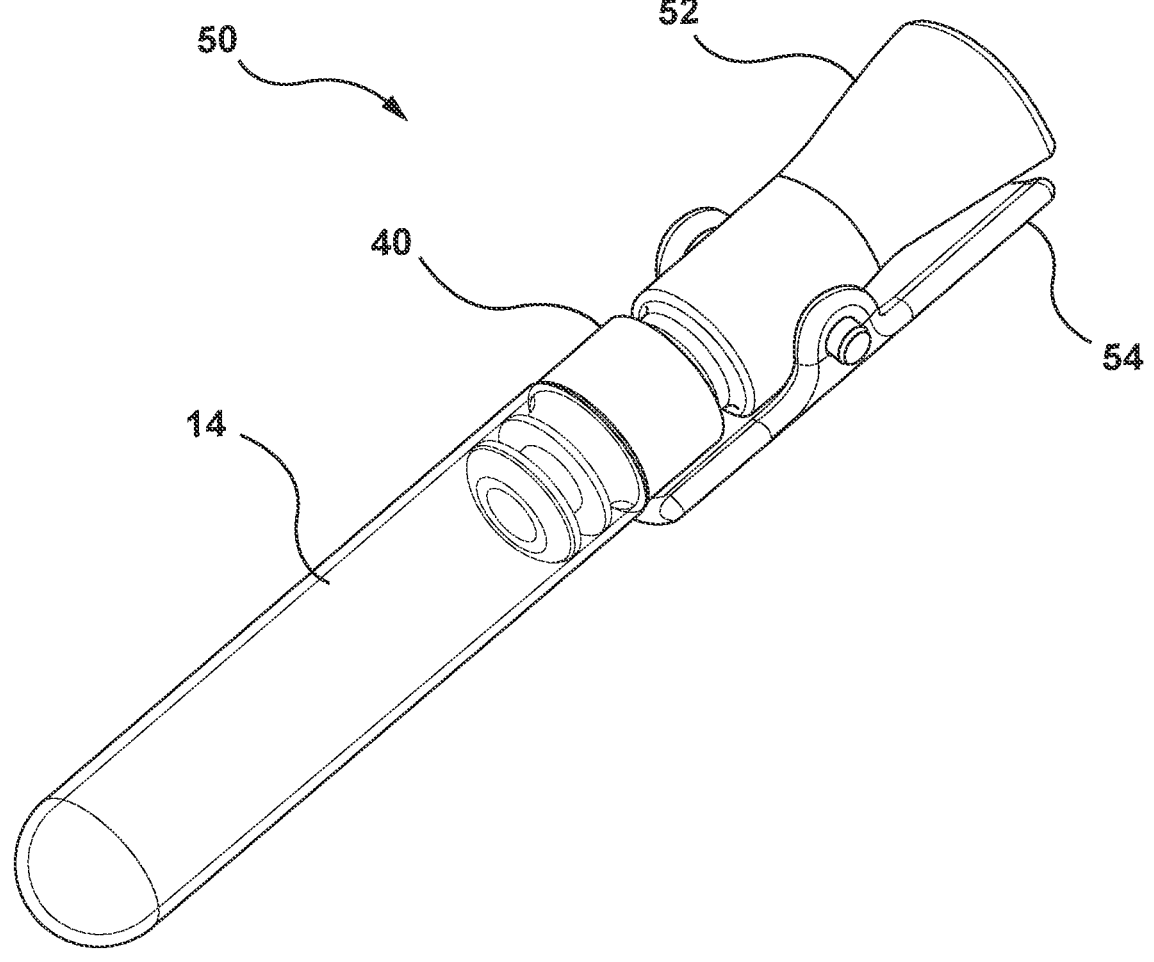
FIG. 5A shows an isometric view of a second insert in a push cap of a round bottom test tube.
Figure 5B:
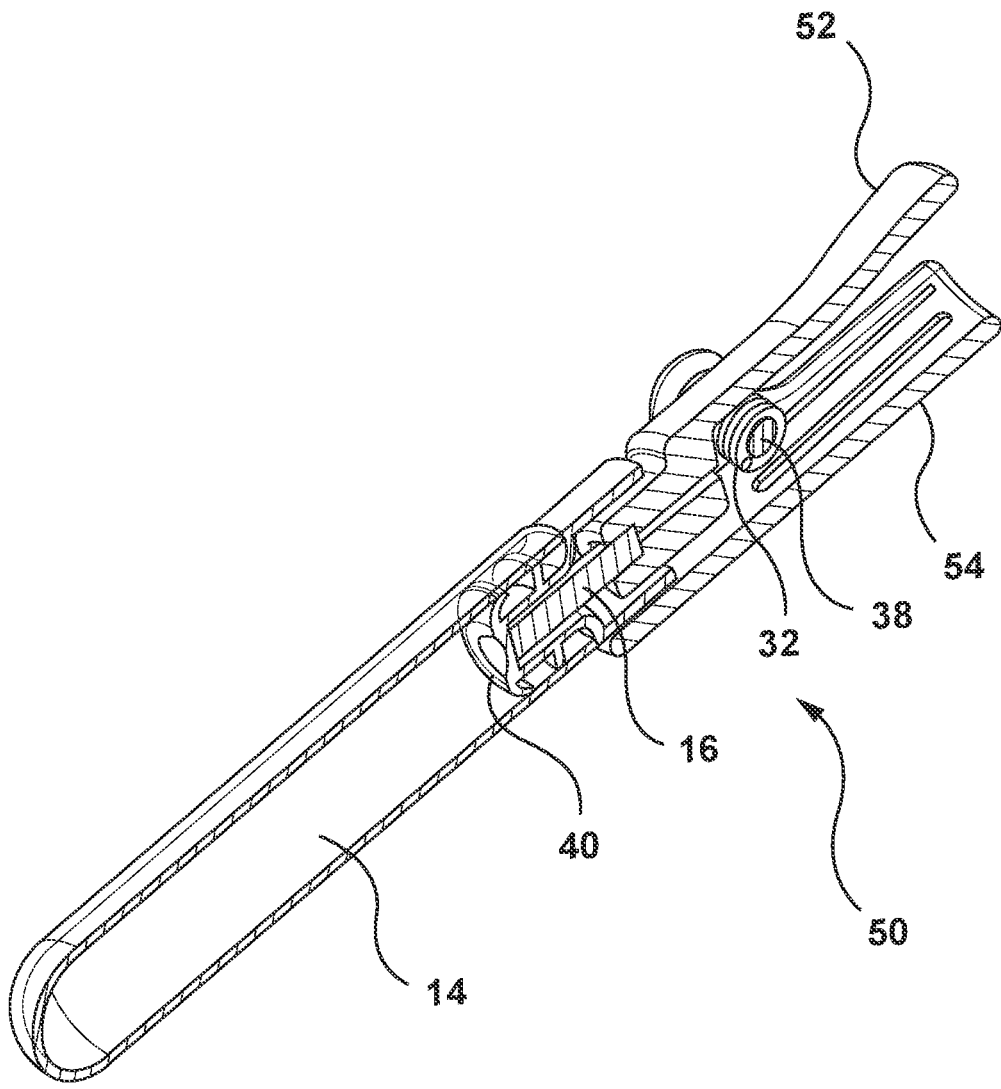
FIG. 5B is a cross section of the insert, cap and tube of FIG. 5A.

FIGS. 5A and 5B shows a second insert 50. The second insert 50 has a first portion 52 and a second portion 54 held together by a pin 38 surrounded by a spring 32. In the position shown, a magnet 16 attached to the first portion 52 is located inside of an internal cap 40. The spring 32 biases the second portion 54 against a side of the protruding part of the internal cap 40. The spring 32 and the second portion 54 thereby hold the first portion 52 and the magnet 16 in the internal cap 40. However, part of the internal cap 40 remains accessible to a user's hands. With the second insert 50 attached to the internal cap 40, the internal cap 40 can be removed from a tube 14 or placed onto a tube 14. However, a person can also squeeze the second portion 54 against the bias of the spring 32 to release the second insert 50 from the internal cap 40. The second insert 50 can then be removed from the internal cap 40, which causes the magnet 16 to also be removed from the internal cap 40. Magnetic beads can be attached to or released from an inner surface of the internal cap 40. As described above, the magnetic beads can be separated from a first solution and, optionally, transferred to a second solution.

Figure 6:
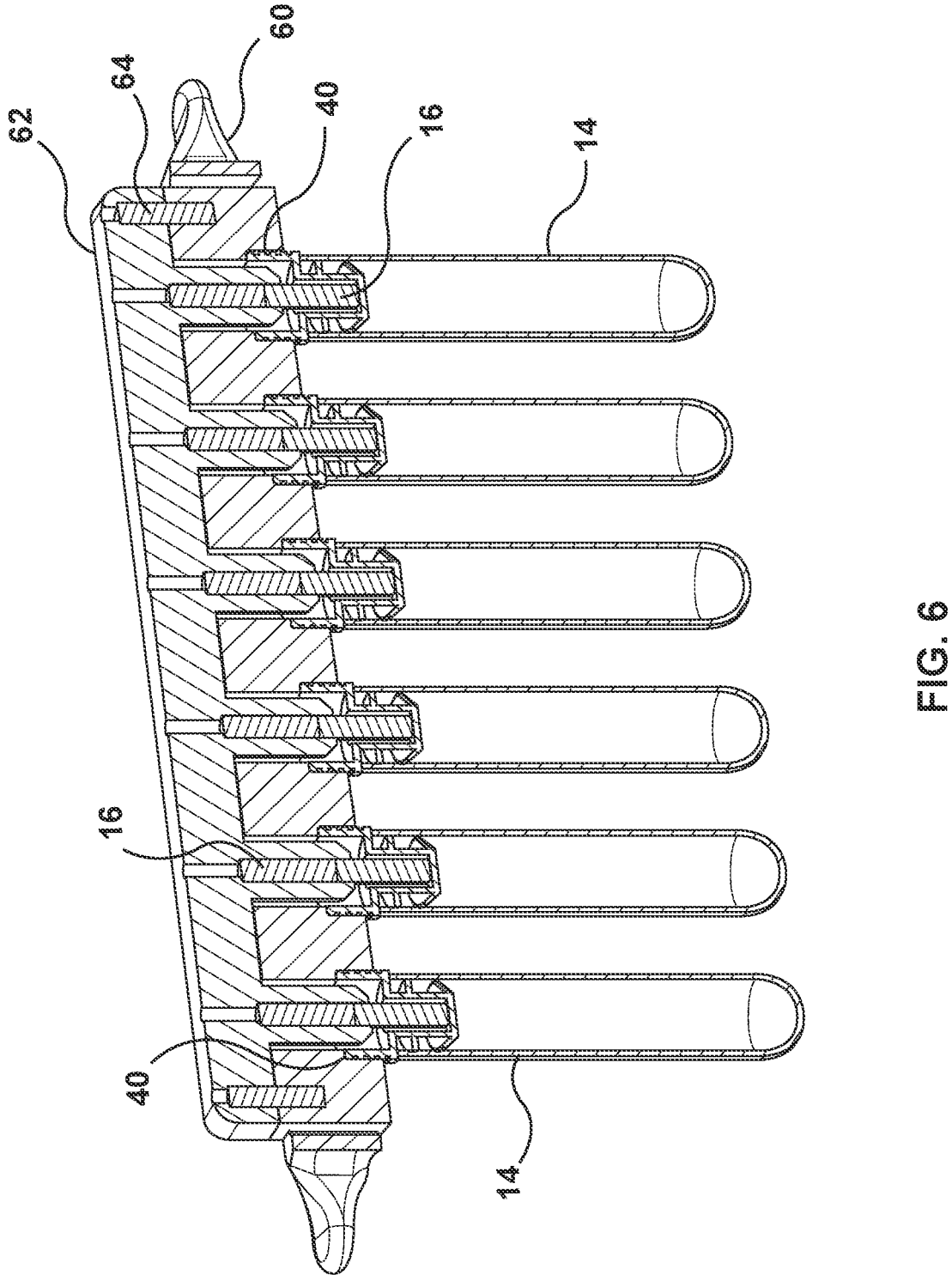
FIG. 6 shows a cross section of a multiple cap holder, a multiple magnet holder, and multiple round bottom test tubes with push caps.
Figure 7:
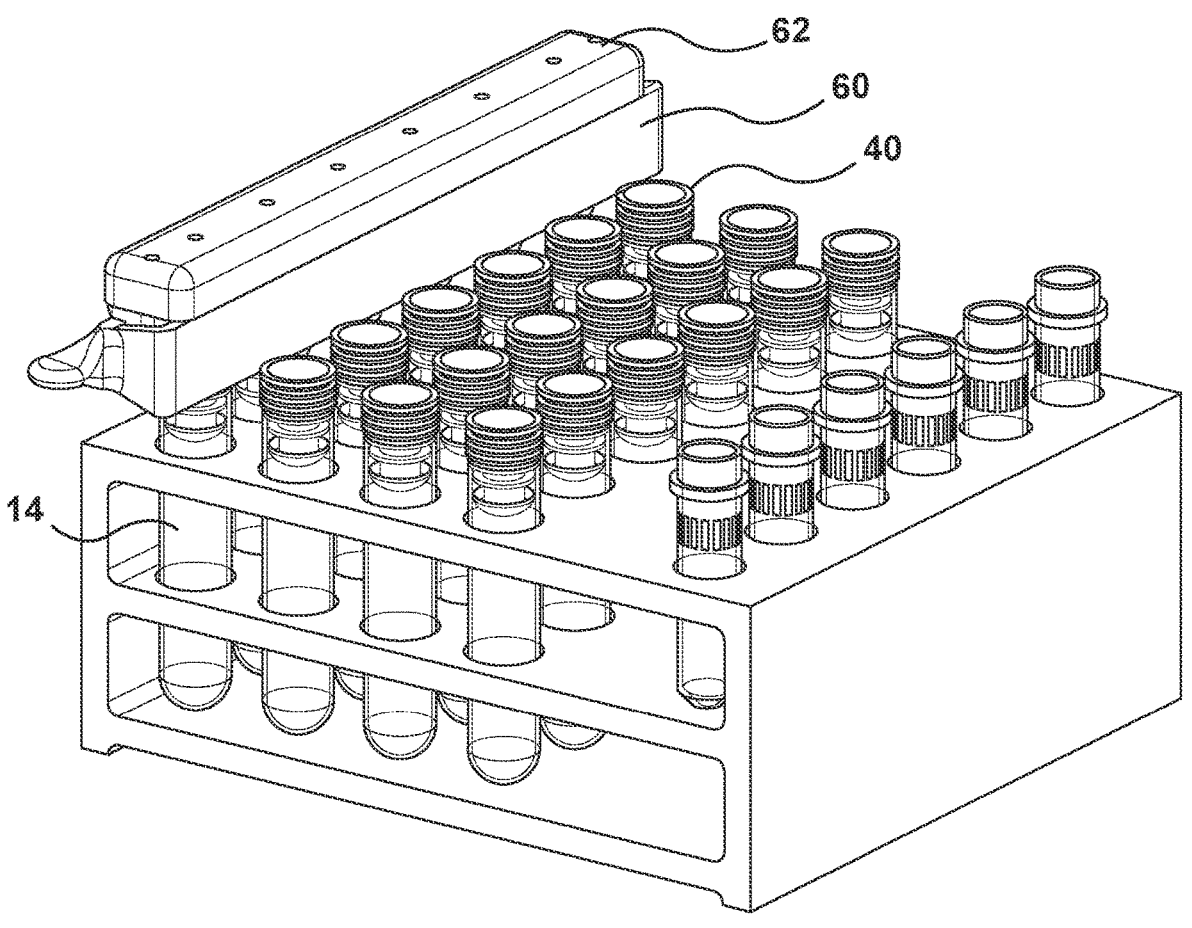
FIG. 7 shows an isometric view of the multiple cap holder and multiple magnet holder, tubes and caps of FIG. 6 and a test tube rack.

FIGS. 6 and 7 shows a multiple cap holder 60 and a multiple magnet holder 62. The multiple cap holder 60 is attached to the multiple magnet holder 62 by way of connecting magnets 64. However, the bond between the connecting magnets 64 can be broken by hand by pulling the multiple magnet holder 62 away from the multiple cap holder 60. Removing the multiple magnet holder 62 also removes magnets 16 from the inside of internal caps 40 attached to the multiple cap holder 60. In the example shown, the caps are internal caps 40 and the multiple cap holder 60 comprises multiple inserts. Alternatively, external caps 12 could be used and the multiple cap holder 60 could form multiple second sleeves 22

When the multiple magnet holder 62 is attached to a multiple cap holder 60, magnets 16 can be placed in multiple internal caps 40 attached to multiple tubes 14. Multiple tubes 14 each containing a magnetic bead suspension are inverted and magnetic beads attach to the multiple internal caps 40. The multiple tubes 14 are then returned to an upright position to separate the magnetic beads from a first solution in each of the multiple tubes 14. Some or all of the multiple tubes 14 can be removed from the internal caps 40 while the internal caps 40 are held in the multiple cap holder 60. New tubes 14 can be placed on the internal caps 40 while the internal caps 40 are held in the multiple cap holder 60. Separating the multiple magnet holder 62 from the multiple cap holder 60 releases the magnetic beads into the new tubes 14. In some examples, a used holds the multiple cap holder 60 in one hand while removing or replacing tubes 14 one by one with their other hand.

Figure 8:
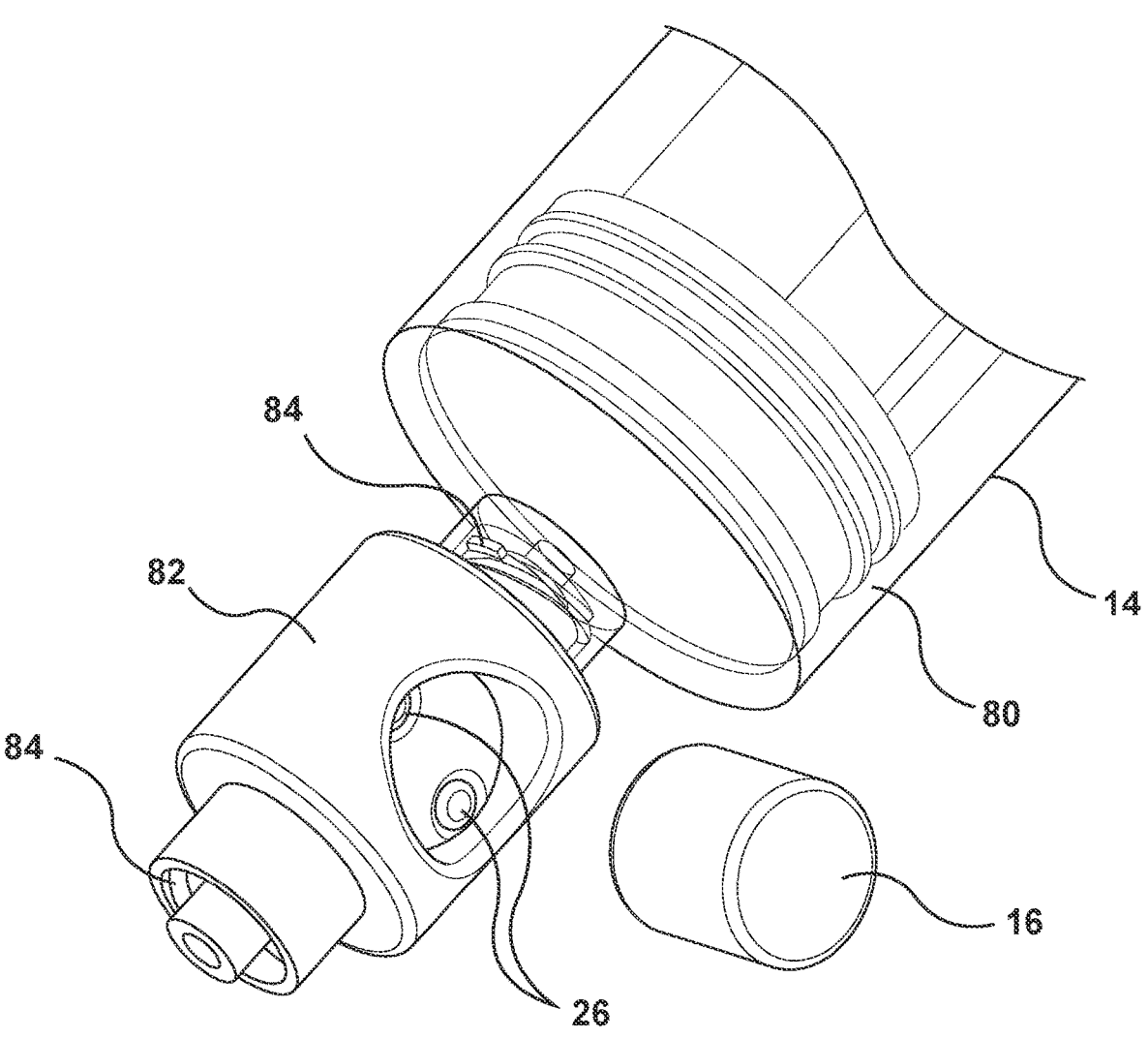
FIG. 8 is an isometric view of a device for extracting magnetic beads in the form of a column attached to a syringe.

FIG. 8 shows another device for separating magnetic beads and/or transferring magnetic beads between tubes. In this example, the tube 14 is part of a syringe 80. A column 82 has fittings 84, for example LUER LOCK™ fittings, on its ends and an internal passageway between the fittings 84. The fitting 84 on one end may be omitted or covered with a cap, allowing the column 82 to function as a cap. The column 82 has one or more metal inserts 26. In the example shown, the metal inserts 26 are rods inserted into cylindrical holes in the column 82. A magnet 16 can be attached to the metal inserts 26 or removed from the metal inserts 26. Alternatively, rather than or in addition to attachment to the metal insert 26, a removable magnet 16 may be screwed, snapped, pushed or otherwise placed into a column 82 or other device. One end of the column 82 can be attached to the syringe 80. The other end of the column may be capped or attached to a tube or needle. In use, a suspension of magnetic beads is drawn into the syringe 80. The suspension may be drawn into the syringe 80 through the column 82 or the column 82 may be attached to the syringe 80 after the suspension is inside the syringe 80. The syringe 80 is inverted and the magnet 16 is placed against the metal inserts 26. Magnetic beads collect in the column 82. The column 82 can then be removed from the syringe 80 with the magnetic beads. The column 82 can then be replaced on the syringe 80 or place onto a new syringe 80. Removing the magnet 16 allows the magnetic beads to be released again into a syringe 80.

In a kit, the column 82 can be moved between syringes 80 of different sizes. For example, a kit may have a relatively large syringe 80 for lysis, a medium sized syringe for washes, and a relatively small syringe for elution. Magnetic beads may be added to a liquid by moving a column 82 with attached magnetic beads to a syringe, and then removing the magnet 16 while sucking the liquid into the syringe. The magnetic beads become suspended in the liquid drawn into the syringe 80. Alternatively, a liquid may be sucked up into a syringe while the column 82 is not on the syringe. The column 82 with magnetic beads is then attached to the syringe. The magnet is removed while expelling the liquid, and the magnetic beads become suspended in the expelled liquid.

Figure 9A:
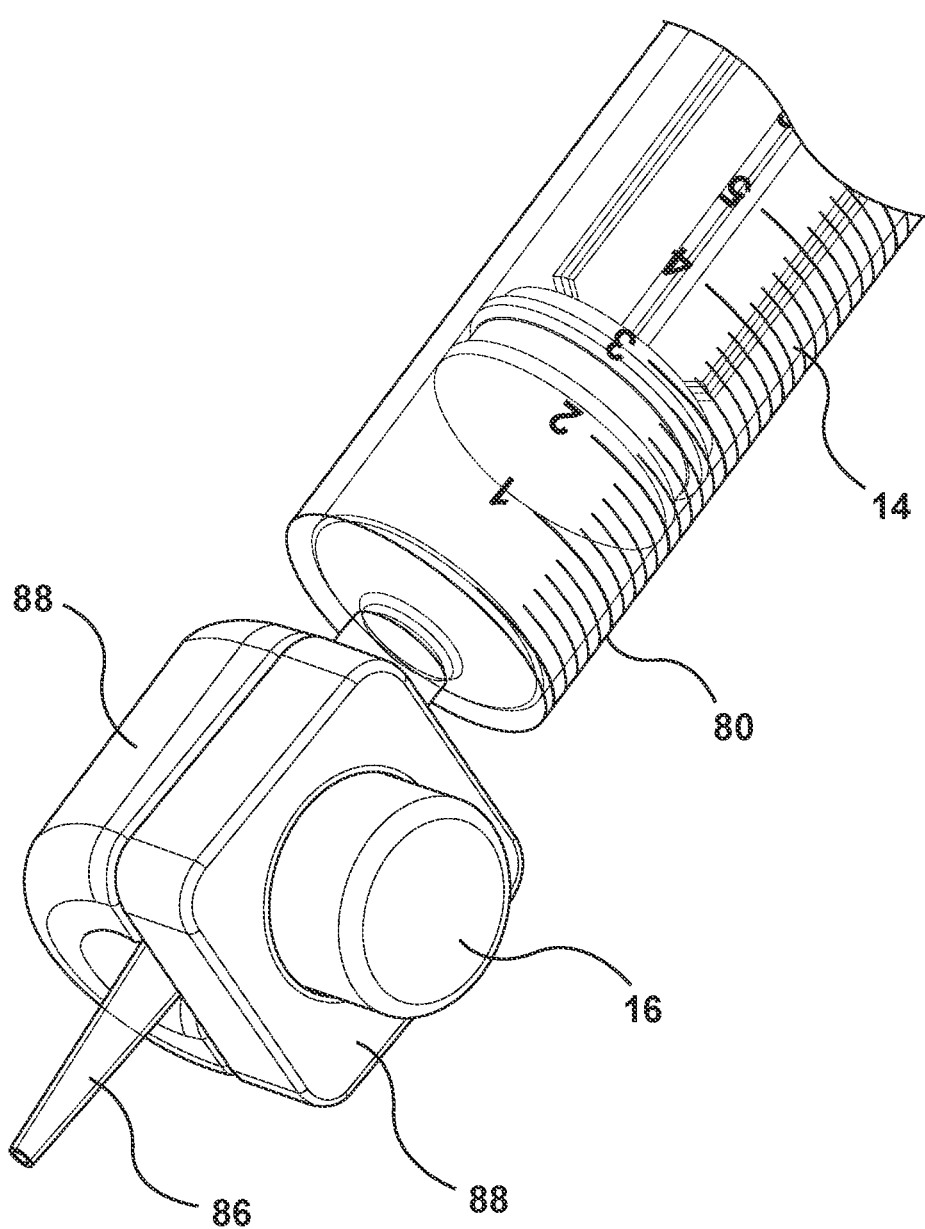
FIG. 9A is an isometric view of a device for extracting magnetic beads on the tip of a syringe.
Figure 9B:
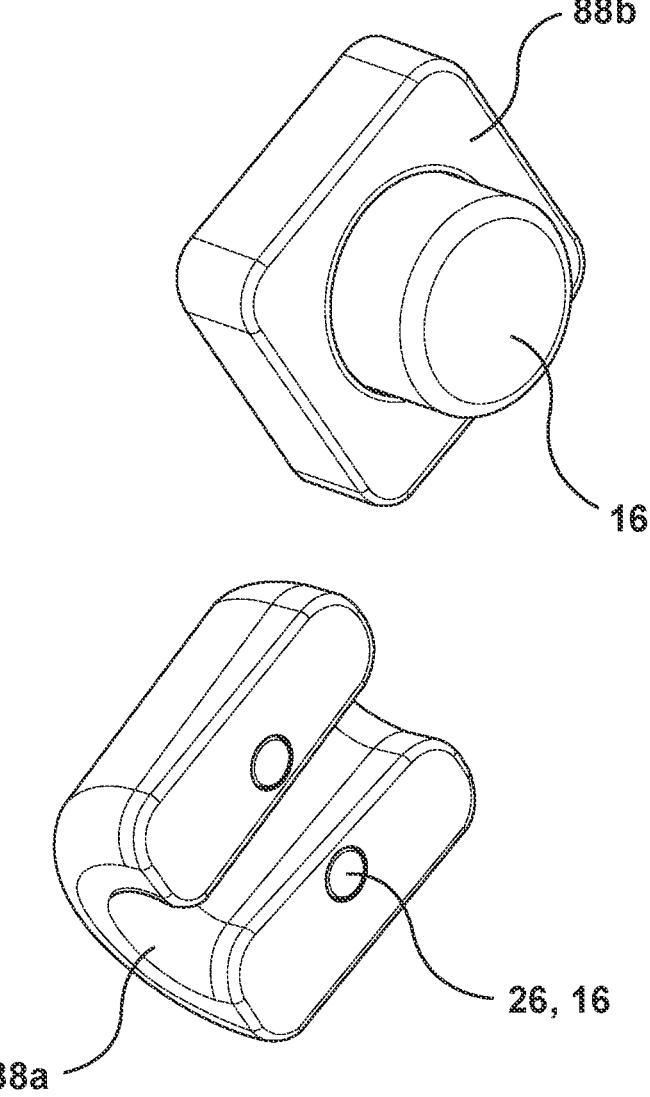
FIG. 9B is an exploded view of the device of FIG. 9A.

FIGS. 9A and 9B show another device in the form of a clip 88 that can be attached around the tip 86 of a syringe 80. On part of the clip 88b has a magnet 16. Another part of the clip 88a has metal inserts 26 or alternatively another magnet 16. When the parts of the clip 88a,b are placed around the tip 86, the magnet 16 holds the clip 88 in place. The magnet 16 is also close enough to the tip 86 to attract magnetic beads in or flowing through the tip 86.

Using the clip 88 or column 82, magnetic beads in a solution can be collected as the solution passes into the syringe 80 or after the solution is in the syringe 80. Removing the magnet 16 releases the magnetic beads back into solution as a solution is ejected from a syringe 80, or as a new solution is drawn into a syringe 80. This approach allows magnetic beads to be quickly processed with multiple solutions in succession relatively easily. For example, a sample is mixed with magnetic beads in a container by repeatedly aspirating and dispensing the sample using the syringe 80. The clip 88 or column 82 and magnet 16 are then applied to collect the magnetic beads inside the column 82 or tip 86. Residual liquid is then pushed out of the syringe 80 leaving only the captured magnetic beads in the column 82 or tip 86. The next solution for processing the magnetic beads is then pulled into the syringe 80 with the magnet 16 removed to release the magnetic beads into the new solution. In this way, the magnetic beads can be washed, and recollected, and this process repeated as many times as necessary.

Figure 11A:
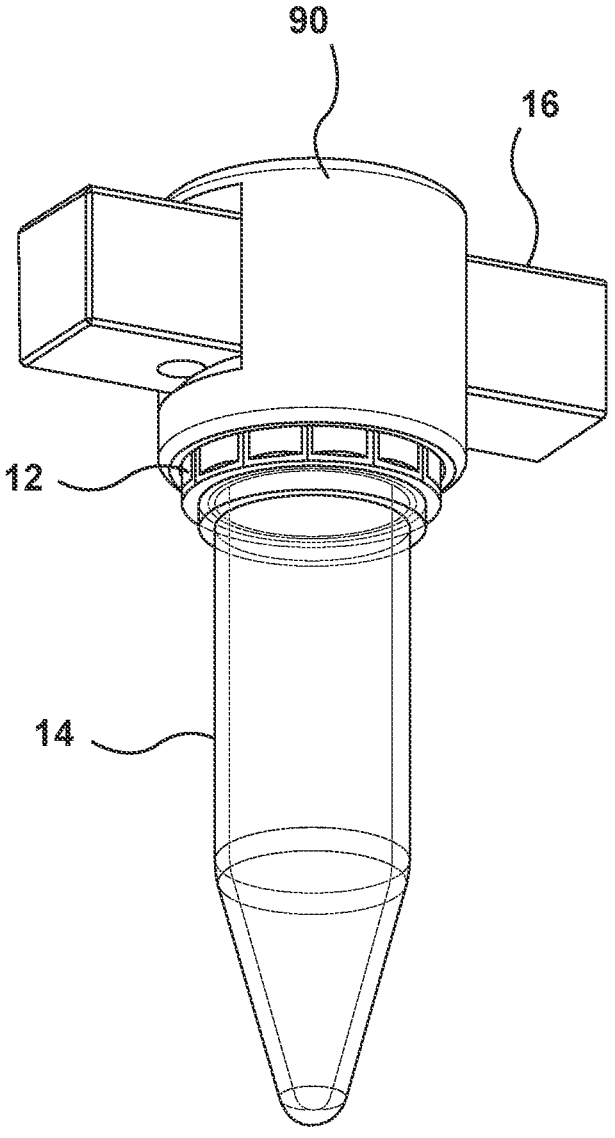
FIG. 11A shows an isometric view of a third sleeve on the screw cap of a conical centrifuge tube with a magnet inserted into the third sleeve.
Figure 11B:
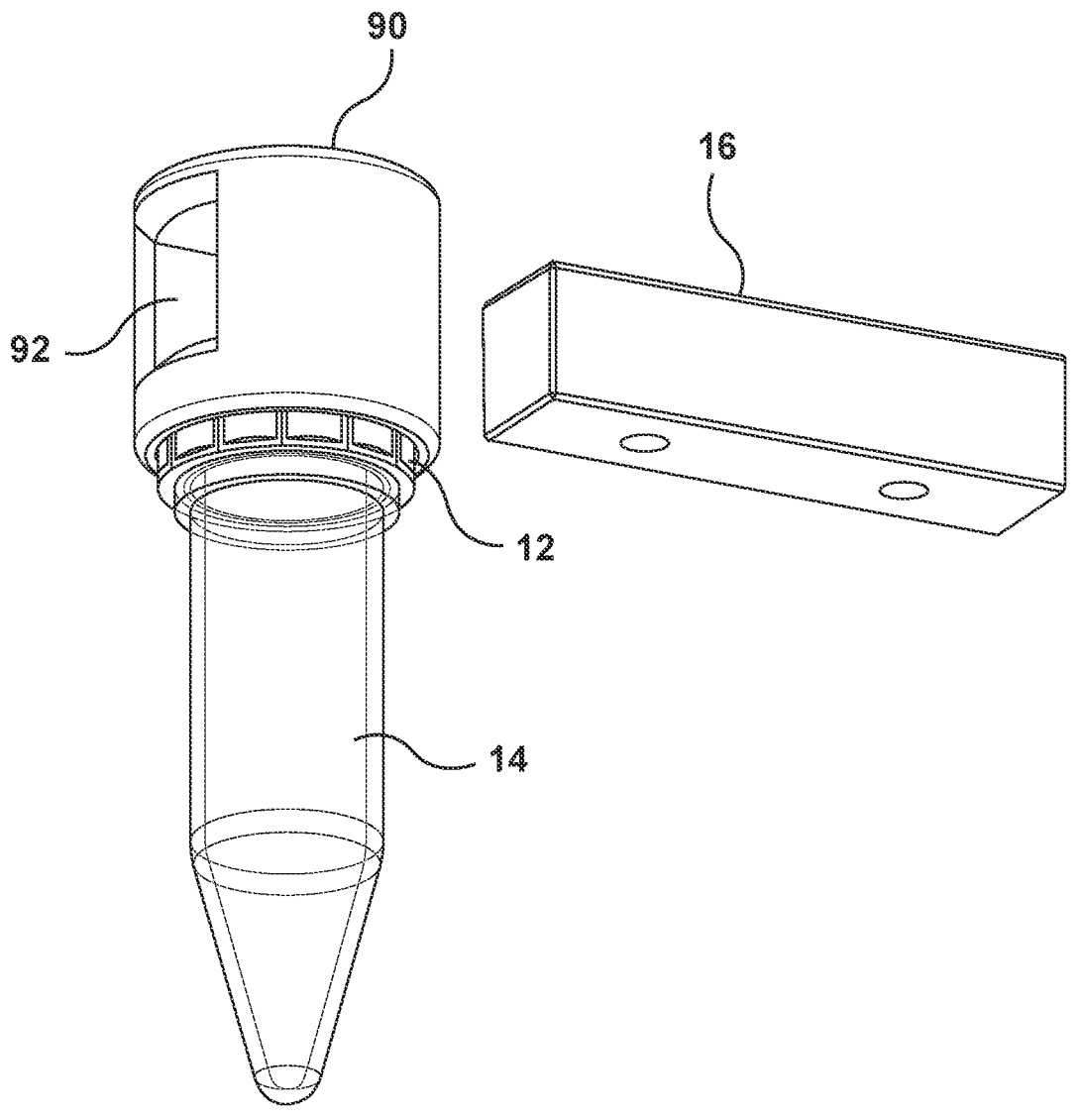
FIG. 11B shows the third sleeve of FIG. 11A with the magnet removed by sliding the magnet out of the third sleeve.

FIGS. 11A and 11B show a third sleeve 90. The third sleeve 90 has a slot 92. A magnet 16 can be slid into or out of the slot 92. The third sleeve 90 with the magnet 16 inserted can be used to unscrew an external cap 12 and move the external cap to another tube 14 with magnetic beads attached. Removing the magnet 16 or the third sleeve 90 releases the magnetic beads into the new tube 14.

Figure 12A:
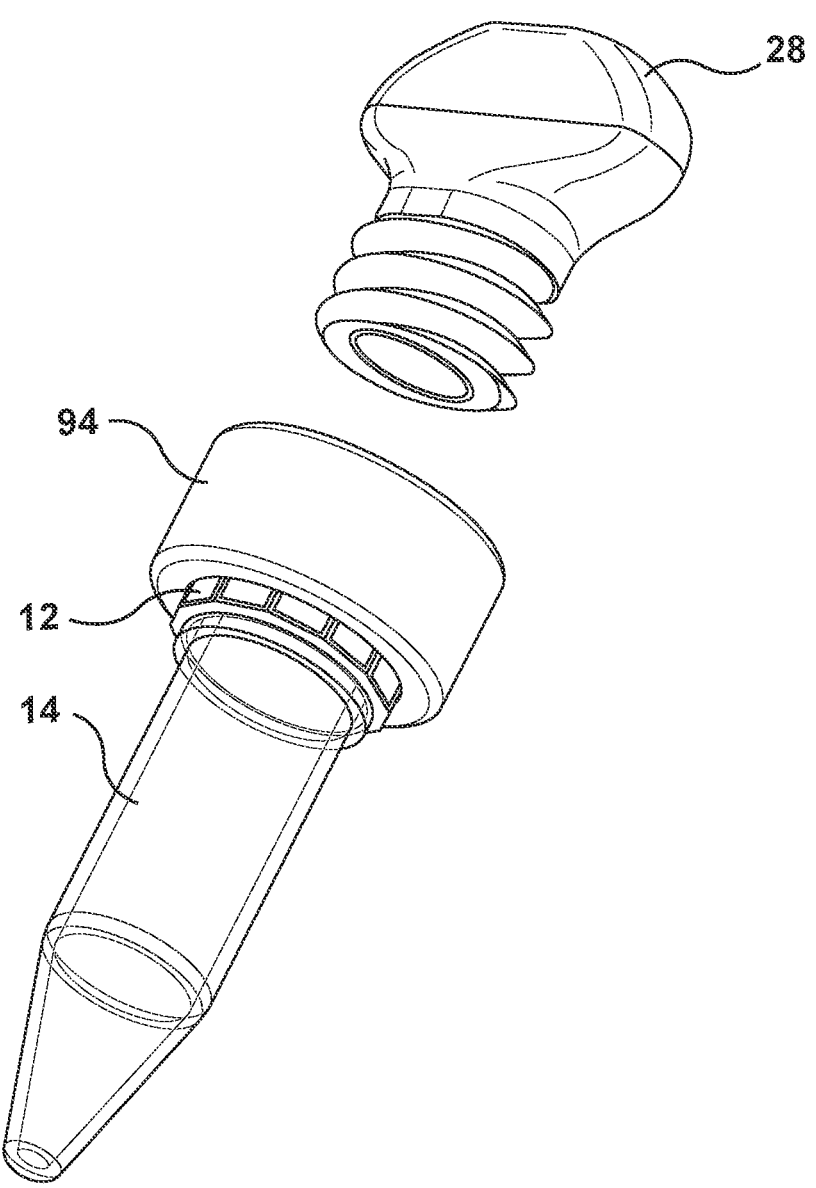
FIG. 12A shows an isometric view of a fourth sleeve with a removable magnet holder unscrewed from the fourth sleeve.
Figures 12B, 12C:
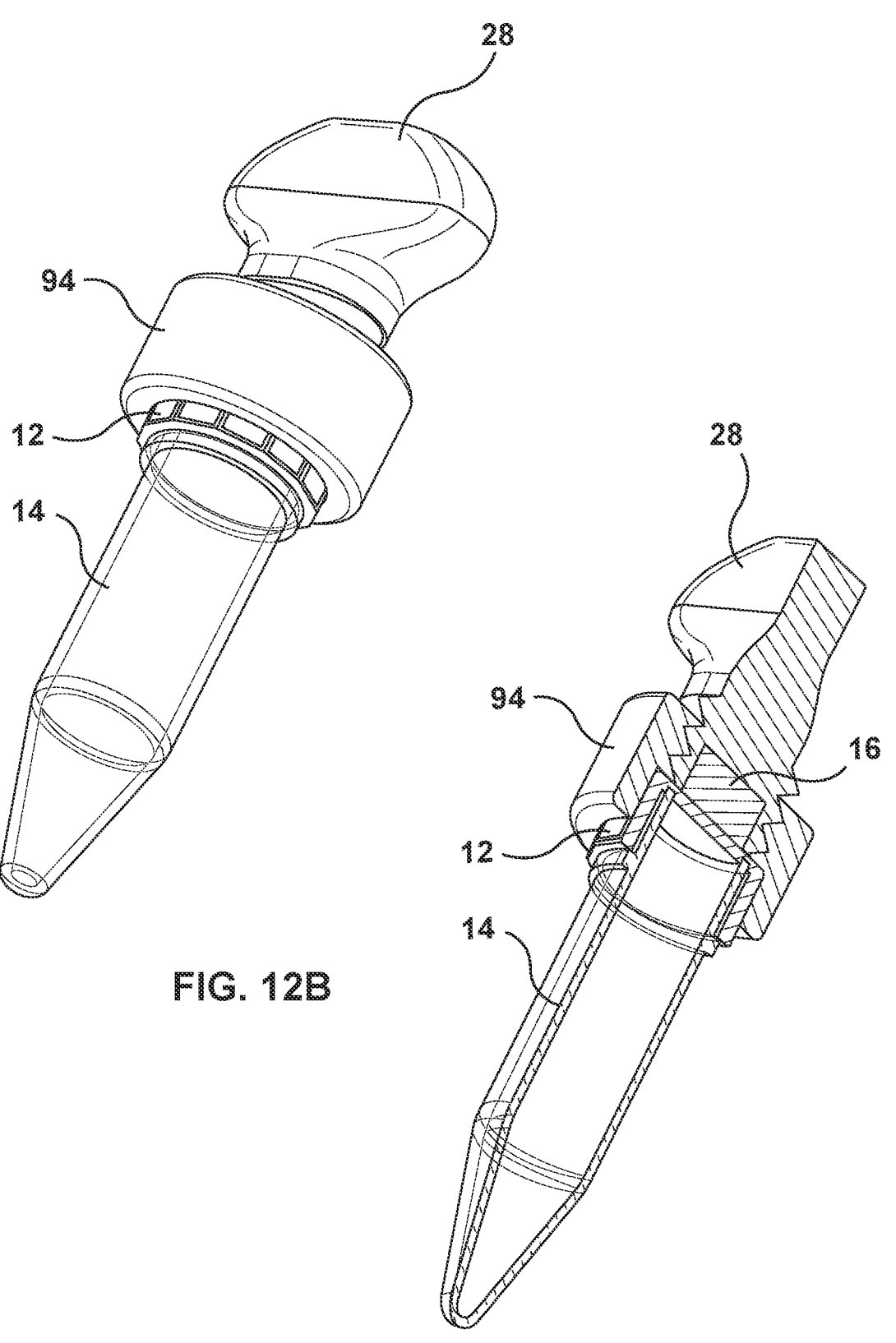
FIG. 12B shows an isometric view of the fourth sleeve of FIG. 12A with the removable magnet holder screwed into the fourth sleeve.
FIG. 12C is a cross section of FIG. 12B

FIGS. 12A, 12B and 12C show a fourth sleeve 94. The fourth sleeve 94 is threaded to receive a similarly threaded magnet holder 28 with a magnet 16. The fourth sleeve 94 with the magnet holder 28 screwed into it can be used to unscrew an external cap 12 and move the external cap to another tube 14 with magnetic beads attached. Removing the magnet holder 28 or the fourth sleeve 94 releases the magnetic beads into the new tube 14.

Figure 13:
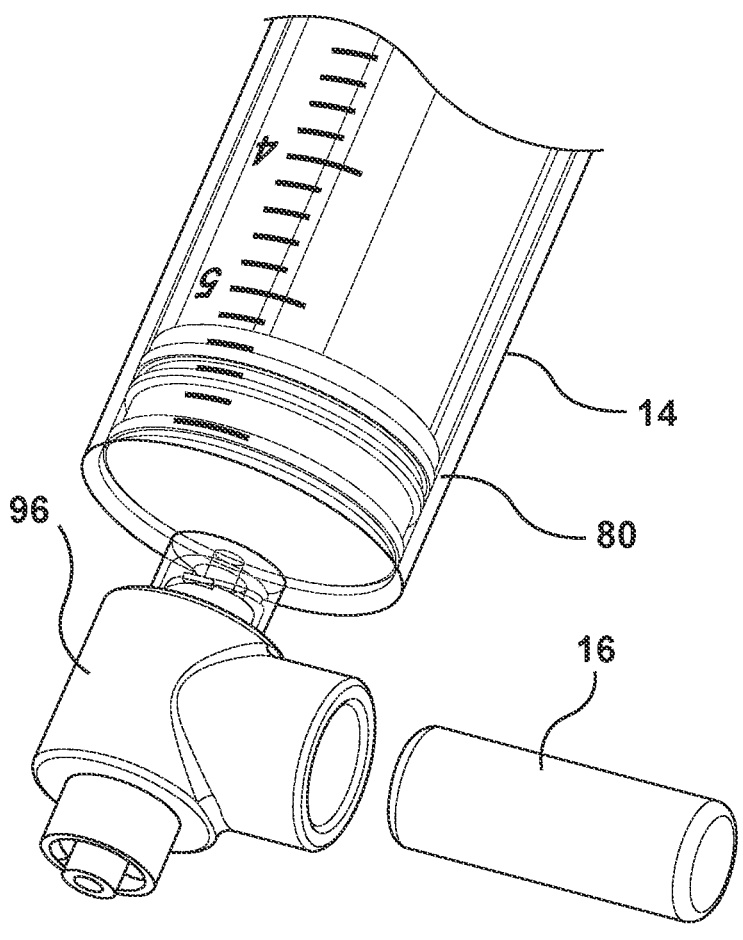
FIG. 13 is an isometric view of another device for extracting magnetic beads in the form of a column attached to a syringe and a removable magnet.
Figure 14:
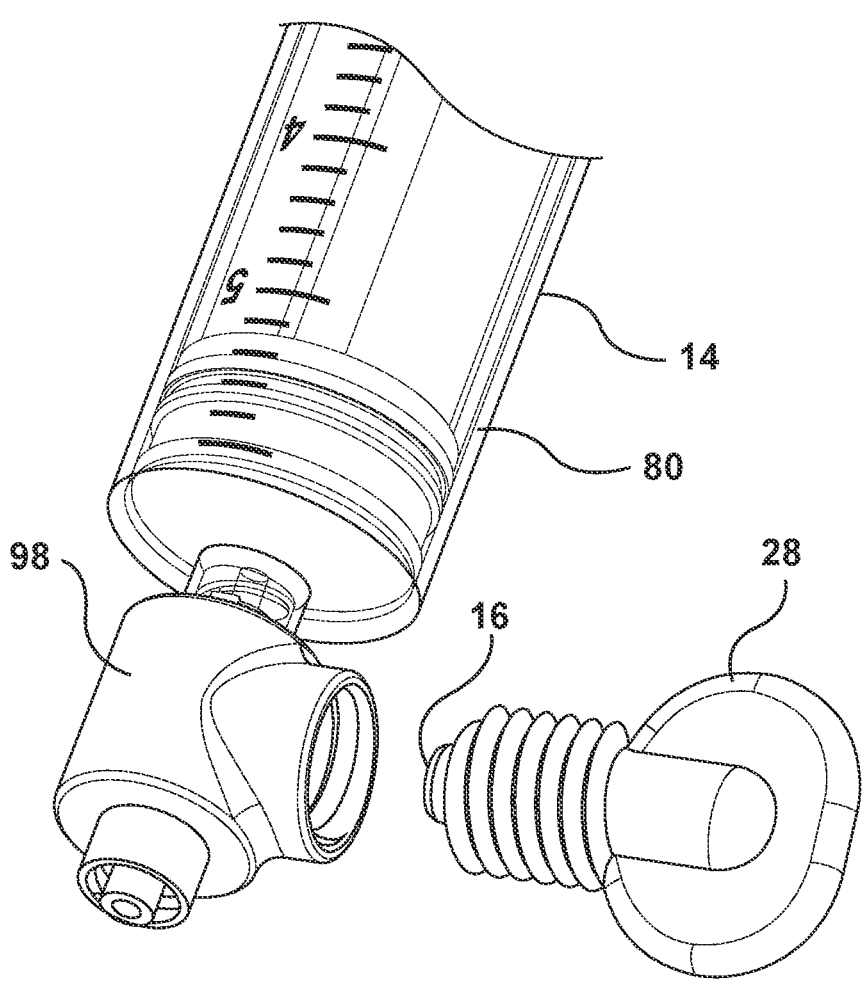
FIG. 14 is an isometric view of another device for extracting magnetic beads in the form of a column attached to a syringe with a removable magnet holder.

FIG. 13 shows a second column 96. The second column 98 receives a magnet 16 that can be slide into or out of the second column 96. FIG. 14 shows a third column 98. The third column 98 receives a magnet holder 28 with magnet 16 that can be screwed into or out of the third column 98. The second column 96 and the third column 98 can be used generally as described for the column 82 of FIG. 8.

Example 1: Wastewater Sampling

A process for extracting RNA from a wastewater sample to test for the presence of SARS-COV-2 RNA is described below. The buffers and other solutions are commercially available from Luminultra Technologies Ltd. The step of preparing tubes can be done at a factory or laboratory. The prepared and capped tubes are then assembled into a kit for use at a testing site. Although the process is described below with a sleeve as in FIG. 1 or 2 and conical tubes having external screw caps, the process may be adapted to use any of the devices described above may be used for separating magnetic beads from a suspension in one tube and moving the magnetic beads to another tube. In the process described below, a safe waste disposal facility is available. However, alternatively waste liquids may be capped in tubes after the tubes have been used and transported to a safe disposal site.

Materials:
COVID-19 Lysis/Binding Buffer Concentrate
COVID-19 Lysis Supplement 1A
COVID-19 Wash Buffer 1
COVID-19 Wash Buffer 2
COVID-19 Elution buffer NA
5 mL Conical Tubes
Magnetic Cap Sleeve
Silica-Coated Magnetic Binding Beads
95-100% Ethanol Procedures:
I. Prepare Tubes
1. Prepare a set of 5 mL tubes containing the following reagents for each sample:

| Tube # | Description | Reagent |
|---|---|---|
| 1 | Lysis | 3 mL of Lysis/Binding Concentrate + 125 μL of Lysis Supplement 1A |
| 2 | Wash 1 | 1 mL Wash Buffer 1 |
| 3 | Wash 2-1 | 1 mL Wash Buffer 2 |
| 4 | Wash 2-2 | 1 mL Wash Buffer 2 |
| 5 | Ethanol | 1 mL 95-100% Ethanol |
| 6 | Elution | 100 μL Elution Buffer NA |

2. Store tubes capped at room temperature until use.
II. Sample Preparation
3. Swirl wastewater sample to resuspend solids and then transfer 0.5 mL of wastewater to Tube #1 (Lysis).
4. Invert tube 5-10 times gently and incubate tube at room temperature for 10 minutes. Invert tube intermittently while incubating.
III. DNA Binding
1. Add 1.75 mL of Ethanol and 50 uL of the Magnetic Binding Beads to Tube #1, cap and invert 5-10 times. Ensure beads are fully resuspended before use by vortex mixing or shaking vigorously.
2. Incubate Tube #1 at room temperature for an additional 10 minutes. Invert tube intermittently while incubating.
3. Apply magnetic sleeve around the cap of the tube and invert the tube to collect the magnetic beads on the inside of the cap. If necessary, use a gentle swirling motion to collect all the beads.
4. Slowly re-invert tube to remove all the liquid from the inside of the cap, leaving only the beads. Remove the cap with attached sleeve (and bound magnetic beads).
IV. Sample Purification
5. Cap Tube #2 (Wash 1) with the sleeve attached to the cap with magnetic beads. After ensuring tube is capped firmly, remove the sleeve and invert tube 10-15 times to resuspend the beads.
6. Repeat steps 3 and 4 and discard the liquid waste from the magnetic beads.
7. Repeat steps 5 and 6 by transferring the cap with attached sleeve to Tube #3 (Wash 2-1), Tube #4 (Wash 2-2), and Tube #5 (Ethanol).
8. Allow cap with attached sleeve and magnetic beads to incubate at room temperature open to the air for 5-10 minutes or until all the ethanol has evaporated from the beads.

V. DNA Elution

9. Cap Tube #6 (Elution) with the sleeve attached to the cap with magnetic beads. After ensuring tube is capped firmly, remove the sleeve and invert tube 10-15 times to resuspend the beads. Incubate on bench for 1-2 minutes.

10. Apply magnetic sleeve around the cap of the tube and invert the tube to collect the magnetic beads on the inside of the cap. If necessary, use a gentle swirling motion to collect all the beads.

11. Slowly re-invert tube to remove all the liquid from the inside of the cap, leaving only the beads. Remove the cap with attached sleeve and close tube with a new cap. The old cap with beads can be discarded. The remaining sample liquid in Tube #6 contains the eluted nucleic acids. If the purified nucleic acids will not be used immediately, store at −20° C. or lower until use.

Modified Procedure:

Tube #6 contains only 100 μL of elution buffer. In some examples an even smaller volume, for example 50 μL, of elution buffer may be used. Optionally, to account for the very low volume of buffer in the elution step, tube 6 may be replaced with a smaller tube that is not pre-loaded with the elution buffer. For example, tube 6 may be replaced with a 2 mL conical microcentrifuge tube. The elution buffer may be provided in a syringe or other container. At the end of step 7, the mixture of magnetic beads and ethanol is poured into the 2 mL tube. Steps 8 to 11 above are then replaced with steps 12 to 16 below.

12. Insert the conical end of the 2 mL tube into the second recess of a first sleeve as in FIG. 1 to collect the beads to the bottom of the tube. While holding the first sleeve in place in the tube, pour out the ethanol.

13. Leave the tube uncapped at room temperature for 10-15 minutes or until all the ethanol has evaporated from the beads.

VI. DNA Elution

14. Add 50 uL elution buffer to the 2 mL tube with the dried magnetic beads, remove the first sleeve, and gently swirl the tube 10 times to release the nucleic acids from the beads into solution.

15. Incubate the tube for 5 minutes at 60° C. (room temperature can be used if an incubator is not available).

16. Re-apply the first sleeve to the bottom of the 2 mL tube to separate the magnetic beads and pour the eluted nucleic acids into another nuclease-free tube or use immediately for RT-qPCR analysis. If the purified nucleic acids will not be used immediately, store at −20° C. or lower until use.

Example 2: DNA Measurement

FIG. 10 is a graph of experimental results showing counts of total prokaryote DNA over a number of qPCR cycles for DNA extracted from corn mash samples using magnetic beads for samples process using a magnetic sleeve as in FIG. 1 and samples processed using a traditional magnetic rack. In this example, microbial DNA was extracted from corn mash samples using a guanidine-based lysis buffer and the crude DNA bound to silica-coated magnetic beads. The beads were processed using the sleeve in FIG. 1 and on a traditional magnetic rack for comparison purposes. The beads were washed using appropriate buffers and the pure DNA finally eluted into nuclease-free water. The purified DNA (20 μL) was then tested in a qPCR assay targeting Total Prokaryotes. The resulting signal for the sleeve was slightly earlier than the magnetic rack showing as good or superior DNA recovery and purity.

Example 3: RNA Concentration and Extraction for Wastewater Testing

A process for extracting RNA from a wastewater sample to test for the presence of SARS-COV-2 RNA is described below. The buffers and other solutions, MagSleeve™, Bead Grinding Tube, Magnetic Binding Beads and GeneWave™ wastewater sampling device are available from Luminultra Technologies Ltd. A passive wastewater sampling device as described in U.S. provisional patent application 63/252,349, filed Oct. 5, 2021, which is incorporated herein by reference, may be used in place of the GeneWave™ sampling device. The step of preparing tubes can be done at a factory or laboratory. The prepared and capped tubes are then assembled into a kit for use at a testing site. The MagSleeve in the process described below is essentially the same as the first sleeve 10 as in FIGS. 1A, 1B and 1C but the process may be adapted to use any of the devices described herein. The caps used in this example have both inner and outer concentric sidewalls and fit on the tube with the sidewall of the tube between the two sidewalls of the cap. In the process described below, a safe waste disposal facility is available. However, alternatively waste liquids may be capped in tubes after the tubes have been used and transported to a safe disposal site.

Materials:

5 and 15 mL Centrifuge Tubes

Lysis/Binding Buffer Concentrate 80 mL

Lysis Supplement 1A (6 mL Vial) 0.5 g

Wash Solution 1 Concentrate 120 mL

Wash Solution 2 Concentrate 40 mL

Nuclease Free Water 55 mL

Magnetic Binding Beads (silica-coated magnetic beads) 2 mL 1000 uL Filtered Pipet Tips 200 uL Filtered Pipet Tips 20 uL Filtered Pipet Tips Tube Rack for 15 mL Tubes MagSleeve Magnetic Rack for 15 mL Tubes Isopropanol (95-100%) (optional)

Ethanol (95-100%)

Adjustable Volume 1000 uL and 200 uL Pipets

Procedures:

The following description will describe testing a single wastewater test. However, multiple tests can optionally be performed simultaneously or consecutively by repeating the steps as required.

Create Wash Buffer 1 by adding 60 mL of isopropanol (or optionally ethanol) to 120 mL of Wash Solution 1 Concentrate. Create Wash Buffer 2 by adding 160 mL of ethanol to 40 mL of Wash Solution 2 Concentrate. Rehydrate vial of Lysis Supplement 1A with 5 mL of Lysis/Binding Buffer Concentrate, optionally mix intermittently for 1 minute by swirling, to create a Lysis Buffer. Pour the entire 5 mL volume of Lysis Buffer into a 15 mL centrifuge tube.

Mix a sample taken from wastewater with the Lysis Buffer. In one example, 1 mL of a liquid wastewater sample (with suspended and/or dissolved solids) is added to the 15 mL centrifuge tube containing the Lysis Buffer. Cap the tube and mix the sample solution, then incubate for 10 minutes at room temperature. After incubating, add 2 mL of ethanol to the tube and mix. In another example, the Lysis Buffer is poured into a Bead Grinding Tube (a tube containing zirconia beads). A filter containing separated matter from wastewater, for example as captured using a GeneWave™ wastewater sampling device from LuminUltra, is added to the Bead Grinding Tube. Shake the Bead Grinding Tube while incubating at room temperature for 2 minutes. Add 4 mL of 100% ethanol followed by 3 mL of nuclease-free water to the bead grinding tube. Mix then let settle for 1 minute. Transfer as much of the liquid in the bead grinding tube, but not the zirconia beads, to a clean 15 mL centrifuge tube.

Suspend the Magnetic Binding Beads, for example by inverting the bottle containing the Magnetic Binding Beads 5 time, shaking vigorously or vortex mixing. Then add 40 uL of the Magnetic Binding Beads to the 15 mL centrifuge tube (containing a portion of wastewater) prepared by either method described above. Mix, then incubate for 10 minutes at room temperature.

After incubation, place the 15 mL centrifuge tube into the magnetic rack to collect the Magnetic Binding Beads on the side of the tube. Pour the supernatant from the tube and discard the supernatant into a waste container. Add 3 mL of Wash Buffer 1 to the tube and mix. After the Magnetic Binding Beads are re-suspended, transfer the Magnetic Binding Beads and Wash Buffer 1 to a clean 5 mL centrifuge tube, for example with a pipette.

Cap the 5 mL centrifuge tube. Add the MagSleeve to the cap before or after adding the cap to the tube. Invert the tube, for example for 30 seconds, to collect the Magnetic Binding Beads against the cap. Optionally re-invert the tube, optionally two or three times or until the Wash Buffer 1 is clear, to collect more, or substantially all, of the Magnetic Binding Beads. Holding the tube upright (cap side up), remove the cap with the MagSleeve still attached to the cap and holding the Magnetic Binding Beads to the cap. Pour out the Wash Buffer 1 into the waste container.

Add 1 mL of Wash Buffer 2 to the 5 mL tube. Add the cap with the MagSleeve and Magnetic Binding Beads to the 5 mL tube. Remove the MagSleeve from the cap and shake vigorously to wash the Magnetic Binding Beads. Replace the MagSleeve on the cap. Invert the tube, for example for 30 seconds, to collect the Magnetic Binding Beads against the cap. Optionally re-invert the tube, optionally two or three times or until the Wash Buffer 2 is clear, to collect more, or substantially all, of the Magnetic Binding Beads. Holding the tube upright (cap side up), remove the cap with the MagSleeve still attached to the cap and holding the Magnetic Binding Beads to the cap. Pour out the Wash Buffer 2 into the waste container. Optionally repeat these steps with an additional 1 mL of Wash Buffer 2.

After removing the Wash Buffer 2, add 1 mL of 100% ethanol to the 5 mL tube. Add the cap with the MagSleeve and Magnetic Binding Beads to the 5 mL tube. Remove the MagSleeve from the cap and shake vigorously to wash the Magnetic Binding Beads. Replace the MagSleeve on the cap. Invert the tube, for example for 30 seconds, to collect the Magnetic Binding Beads against the cap. Optionally re-invert the tube, optionally two or three times or until the ethanol is clear, to collect more, or substantially all, of the Magnetic Binding Beads. Holding the tube upright (cap side up), remove the cap with the MagSleeve still attached to the cap and holding the Magnetic Binding Beads to the cap. Pour out the ethanol into the waste container.

Place the MagSleeve and cap with Magnetic Binding Beads on a level surface with the Magnetic Binding Beads facing up. Remove any excess ethanol if possible from the cap, for example with a P100 pipette, but without removing Magnetic Binding Beads. Let the Magnetic Binding Beads dry out, for example for 5-15 minutes and/or until the Magnetic Binding Beads assume a light color or otherwise appear dry.

To elute RNA from the Magnetic Binding Beads, add 100 uL of Nuclease-Free Water directly to the dried Magnetic Binding Beads inside the cap. Attach the cap with the MagSleeve and rehydrated Magnetic Binding Beads to a clean 5 mL tube. After capping the tube, remove the MagSleeve and remove the Magnetic Binding Beads from the cap, for example by tapping the tube or cap against a solid surface 2-3 times. Shake the Magnetic Binding Beads to the bottom of the 5 mL tube, for example using a downward thrust motion. Heat the tube to 65° C., for example in a dry bath, and incubate for 3 minutes. After incubation, invert the tube and shake the Magnetic Binding Beads back into the cap. Apply the MagSleeve to the cap, either before or after shaking the Magnetic Binding Beads into the cap. Remove the cap, with MagSleeve and Magnetic Binding Beads, and place the cap on a level surface with the Magnetic Binding Beads facing upwards. Remove, for example with a pipette, free liquid from the cap. The liquid contains eluted RNA. The liquid with eluted RNA can be transfer to a 1.5 mL elution tube, or directly into a lyophilized PCR strip tube for immediate analysis. Alternately, eluted RNA can be stored at −20° C. for short periods of time or at −80° C. for longer than 2 weeks.

We claim:

1. A magnetic bead separation device comprising, a sleeve having a first recess adapted to fit over some or all of an external sidewall of a cap of a liquid sample tube; and,
a magnet attached or attachable to the sleeve
wherein the sleeve has a second recess adapted to receive the closed end of a tube of the same or different size.

2. The device of claim 1 having a detachable magnet.

3. The device of claim 2 having a metal insert, wherein the detachable magnet selectively connects to the metal insert.

4. The device of claim 2 wherein the detachable magnet is screwed, snapped or pushed into the sleeve.

5. The device of claim 1 wherein the first recess of the sleeve is adapted to provide a press fit over the cap.

6. The device of claim 1 wherein the sleeve comprises an elastic material.

7. The device of claim 1 wherein the cap may be removed from a tube with the sleeve attached to the cap.

8. The device of claim 1 further comprising a plurality of tubes, each of the plurality of tubes pre-filled with a reagent required for an assay.

9. The device of claim 8 wherein each of the plurality of tubes accepts the same cap.

10. The device of claim 8 comprising magnetic beads.

11. The device of claim 1 wherein the second recess is conical.

12. A process for conducting a biological assay comprising steps of,
drawing a first liquid comprising a suspension of magnetic beads and a first reagent into a syringe; and,
expelling the first liquid from the syringe,
putting a removable column comprising a magnet inline with the syringe while drawing or expelling the first liquid, or between drawing and expelling the first liquid, whereby at least some of the magnetic beads are separated from the suspension and retained in the removable column.

* * * * *